United States Patent
Kong et al.

(10) Patent No.: US 10,163,268 B2
(45) Date of Patent: Dec. 25, 2018

(54) MOBILE TERMINAL AND OPERATING METHOD THEREOF

(71) Applicant: LG ELECTRONICS INC., Seoul (KR)

(72) Inventors: Hyesoo Kong, Seoul (KR); Jeonghwa Yang, Seoul (KR); Jungchul Kim, Seoul (KR); Yeojeong So, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/385,609

(22) Filed: Dec. 20, 2016

(65) Prior Publication Data
US 2018/0033205 A1   Feb. 1, 2018

(30) Foreign Application Priority Data

Aug. 1, 2016   (KR) .................. 10-2016-00975858

(51) Int. Cl.
| G09G 5/00 | (2006.01) |
| G06T 19/00 | (2011.01) |
| G06K 9/00 | (2006.01) |
| G06T 11/60 | (2006.01) |
| A61B 5/00 | (2006.01) |
| A61B 5/107 | (2006.01) |
| G06F 19/00 | (2018.01) |
| H04W 88/06 | (2009.01) |

(52) U.S. Cl.
CPC .......... *G06T 19/006* (2013.01); *A61B 5/1077* (2013.01); *A61B 5/442* (2013.01); *A61B 5/7275* (2013.01); *A61B 5/7425* (2013.01); *G06F 19/00* (2013.01); *G06K 9/00288* (2013.01); *G06T 11/60* (2013.01); *H04W 88/06* (2013.01)

(58) Field of Classification Search
CPC ....... G06T 19/006; G06T 19/00; G06F 3/011; G06F 3/012; G02B 27/017
USPC .......................................................... 345/633
See application file for complete search history.

(56) References Cited

U.S. PATENT DOCUMENTS

| 8,646,000 B2 * | 2/2014 | Kang | ................... G06F 3/0482 |
| | | | 345/633 |
| 2004/0046736 A1 * | 3/2004 | Pryor | .................................. 3/2 |

(Continued)

FOREIGN PATENT DOCUMENTS

| KR | 101522730 | 5/2015 |
| KR | 101586225 | 1/2016 |
| KR | 101641268 | 7/2016 |

OTHER PUBLICATIONS

PCT International Application No. PCT/KR2016/013293, International Search Report dated Apr. 27, 2017, 3 pages.

*Primary Examiner* — Ke Xiao
*Assistant Examiner* — Gordon Liu
(74) *Attorney, Agent, or Firm* — Lee, Hong, Degerman, Kang, & Waimey

(57) ABSTRACT

A mobile terminal includes: a wireless communication unit; a display; and a controller configured to receive location information from an auxiliary device via the wireless communication unit, wherein the location information includes curvature information of a part of a face of a user that is in contact with the auxiliary device and movement information of the auxiliary device relative to the user; recognize a part of the face based on the location information; and cause the display to display the recognized part of the face in real time.

17 Claims, 26 Drawing Sheets

(56) References Cited

U.S. PATENT DOCUMENTS

| | | | |
|---|---|---|---|
| 2006/0044307 A1* | 3/2006 | Song | G06Q 10/06 345/419 |
| 2007/0035815 A1* | 2/2007 | Edgar | A61B 5/0064 359/359 |
| 2008/0141478 A1* | 6/2008 | Gatzemeyer | A46B 15/0002 15/167.1 |
| 2009/0025747 A1* | 1/2009 | Edgar | A45D 44/005 132/320 |
| 2011/0161861 A1* | 6/2011 | Abramson | G01C 21/367 715/781 |
| 2012/0067364 A1* | 3/2012 | Wong | A45D 44/005 132/200 |
| 2015/0279044 A1 | 10/2015 | Kim et al. | |
| 2016/0125228 A1* | 5/2016 | Son | G06F 19/345 382/118 |

* cited by examiner

FIG. 2
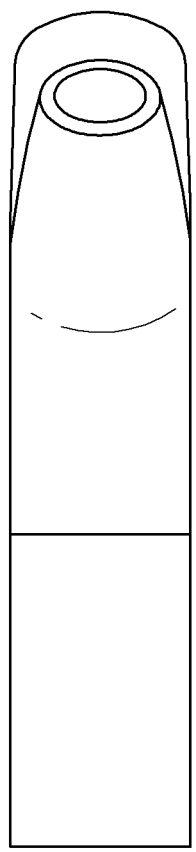
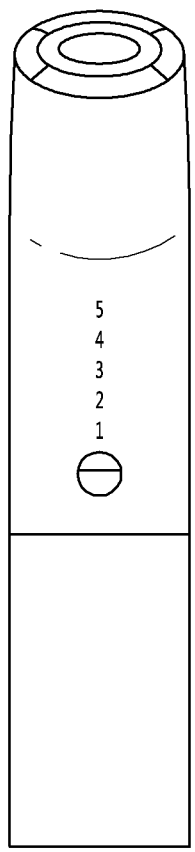
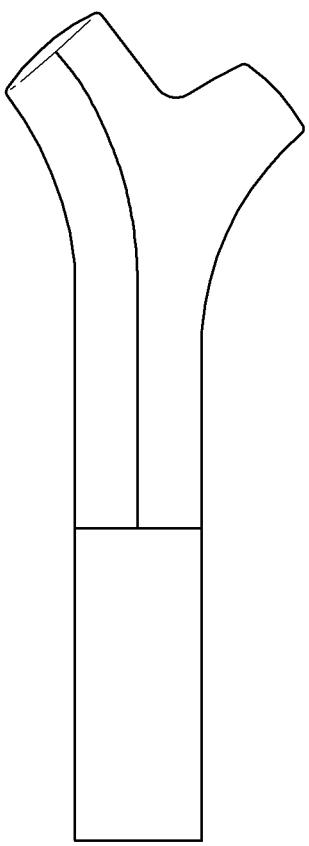
(a)                                    (b)

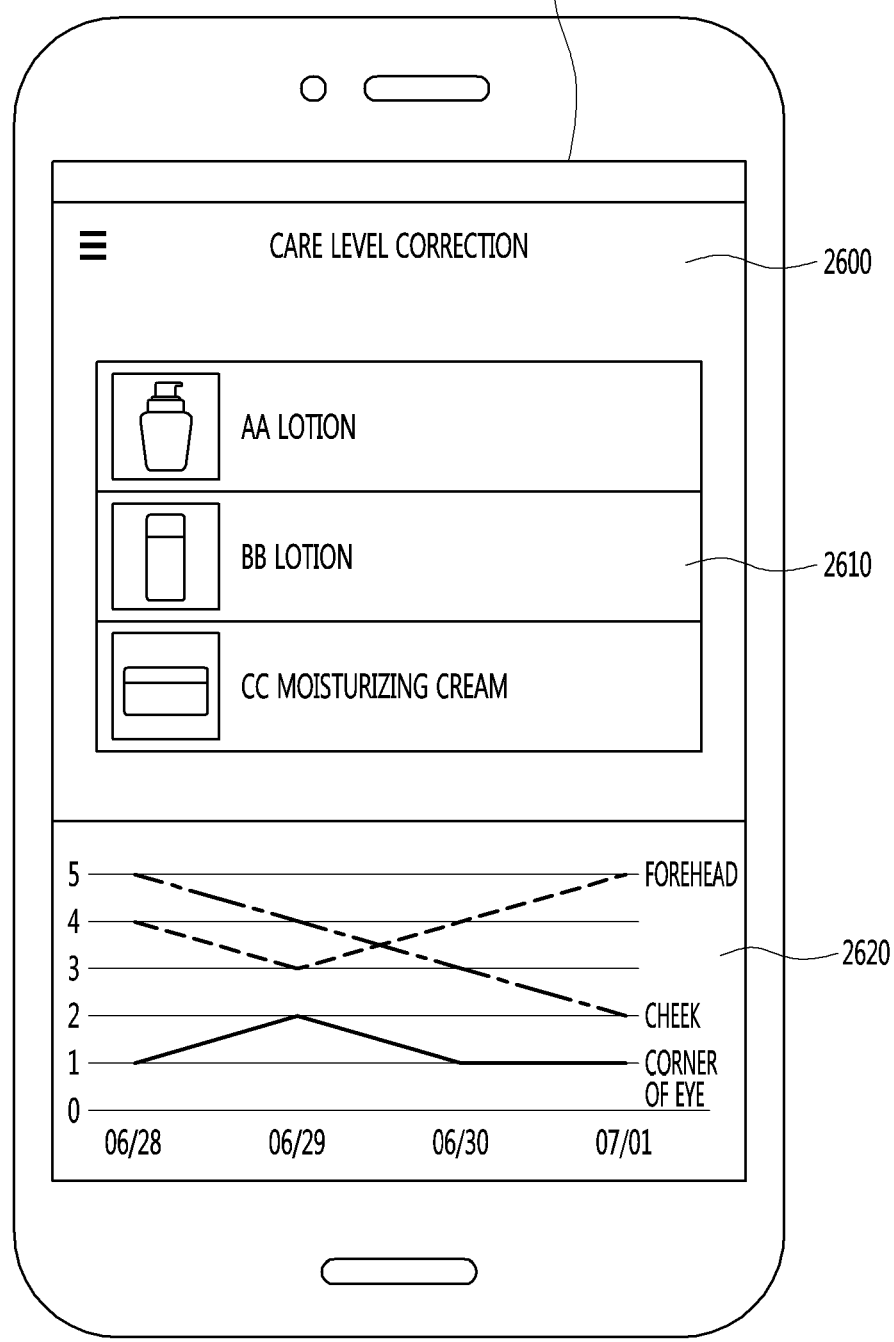

MOBILE TERMINAL AND OPERATING METHOD THEREOF

CROSS-REFERENCE TO RELATED APPLICATIONS

Pursuant to 35 U.S.C. § 119(a), this application claims the benefit of earlier filing date and right of priority to Korean Patent Application No. 10-2016-0097858 filed on Aug. 1, 2016, the entire contents of which are hereby incorporated by reference herein its entirety.

TECHNICAL FIELD

The present disclosure relates to a mobile terminal and an operating method thereof, and more specifically, to a mobile terminal, which is capable of interoperating with a beauty device, and an operating method thereof.

BACKGROUND

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such functions become more diversified, the mobile terminal can support more complicated functions such as capturing images or video, reproducing music or video files, playing games, receiving broadcast signals, and the like. By comprehensively and collectively implementing such functions, the mobile terminal may be embodied in the form of a multimedia player or device.

Efforts are ongoing to support and increase the functionality of mobile terminals. Such efforts include software and hardware improvements, as well as changes and improvements in the structural components.

Meanwhile, the mobile terminal can interoperate with a plurality of mobile terminals to exchange data with the plurality of mobile terminals. Also, the mobile terminal can interoperate with an auxiliary device (e.g., a beauty device) to exchange data with the auxiliary device. The beauty device may refer to a device that is capable of measuring a skin condition of a user or providing a skin care function. Also, the skin care function may include at least one of pore tightening, moisture supply, pilling, ultrasonic stimulation, high-frequency stimulation, and cleansing.

However, in the related art, when the user uses the skin care function, the user has to follow an instruction displayed on the mobile terminal. Also, when the user uses the beauty device, the user cannot know the degree of progress of a care operation for each part of a face. Thus, it is difficult to perform a uniform care operation on the entire face.

SUMMARY

Embodiments provide a mobile terminal, which is capable of measuring a skin condition, performing a care operation, and automatically senses a part of a face, on which a care operation is performed, through a beauty device, and an operating method thereof.

Embodiments also provide a mobile terminal, which is capable of notifying a user of a part of face, on which a care operation is performed through a beauty device, in real time, and an operating method thereof.

Embodiments also provide a mobile terminal, which is capable of providing a guide screen for guiding a care operation and notifying a user of whether the care operation is exactly performed in accordance with the guide screen, in real time, and an operating method thereof.

Embodiments also provide a mobile terminal, which senses a part of a face, on which a care operation is not completed, and displays a message indicating that the corresponding part of the face is required to be further cared, and an operating method thereof.

Embodiments also provide a mobile terminal, which automatically corrects a care level in consideration of care frequency, weather, dermatological treatment, used cosmetics, and the like, and an operating method thereof.

In one embodiment, a mobile terminal includes: a wireless communication unit; a display; and a controller configured to receive location information from an auxiliary device via the wireless communication unit, wherein the location information includes curvature information of a part of a face of a user that is in contact with the auxiliary device and movement information of the auxiliary device relative to the user; recognize a part of the face based on the location information; and cause the display to display the recognized part of the face in real time.

The controller is further configured to cause the to display a care progress status on a simulated face in an overlapping manner, the care progress status mark indicating an area of the face through which the auxiliary device passes.

Opacity of the care progress status is displayed differently based on a number of times the auxiliary device passes over a certain area of the face.

The opacity of the care progress status gets darker as the number of times of the auxiliary device passes over the certain area increases.

The opacity of the care progress status is displayed differently to indicate how much care is required for the face.

The controller is further configured to cause the display to display an area of the face requiring high-intensity care with light opacity; and display an area of the face requiring low-intensity care with dark opacity.

The controller is further configured to cause the display to display the care progress status distinguishably for different parts of the face when the part of the face, at which the auxiliary device is located, is changed.

The controller is further configured to cause the display to display a care guide line on the simulation face, the care guide line indicating a recommended care method for parts of the face.

The controller is further configured to cause the display to display a care location mark at a first position of a simulation face, the care location mark indicating a current location of the beauty device; and care location mark at a second position of the simulation face in response to an input for selecting the care location mark displayed at the first position, the input comprising dragging to and dropping the selected care location mark at the second position.

The controller senses that the auxiliary device has not been moved for more than a threshold period of time, and if the controller senses that the auxiliary device has been moved for more than the threshold period of time, the display displays a notification message indicating that care of the part of the face has not been completed.

The details of one or more embodiments are set forth in the accompanying drawings and the description below. Other features will be apparent from the description and drawings, and from the claims.

BRIEF DESCRIPTION OF THE DRAWINGS

FIG. 2 is a diagram of a beauty device in accordance with an embodiment of the present invention.

FIG. 26 is a diagram for describing a care level correction screen based on cosmetics used by a user in accordance with an embodiment of the present invention.

DETAILED DESCRIPTION OF THE EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1:
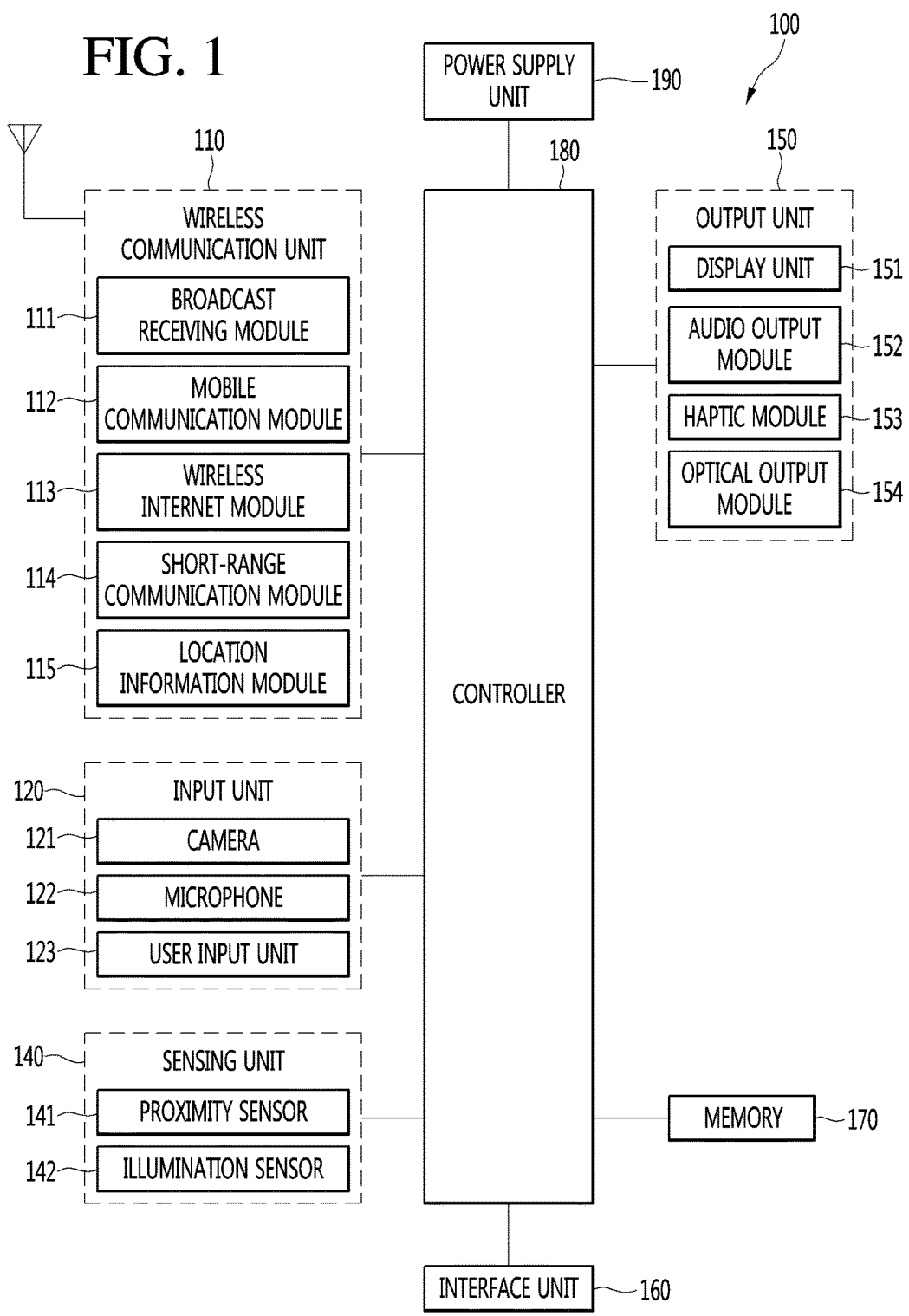
FIG. 1 is a block diagram of a mobile terminal in accordance with the present disclosure.

FIG. 1 is a block diagram of a mobile terminal in accordance with the present disclosure.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1, or activating application programs stored in the memory 170. As one example, the controller 180 controls some or all of the components illustrated in FIG. 1 according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 1, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The broadcast managing entity may be a server which generates and transmits a broadcast signal and/or broadcast associated information, or a server which receives a pre-generated broadcast signal and/or broadcast associated information, and sends such items to the mobile terminal.

The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this case, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the wireless Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 100. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sensing unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term "thumbnail" may be used to refer to a reduced image or a reduced still image. A generated left image thumbnail and right image thumbnail may be displayed with a horizontal distance difference there between by a depth corresponding to the disparity between the left image and the right image on the screen, thereby providing a stereoscopic space sense.

A left image and a right image required for implementing a 3D stereoscopic image may be displayed on the stereoscopic display unit using a stereoscopic processing unit. The stereoscopic processing unit can receive the 3D image and extract the left image and the right image, or can receive the 2D image and change it into a left image and a right image.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the mobile terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

A communication system which is operable with the variously described mobile terminals will now be described in more detail. Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system. A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites.

A broadcasting transmitter (BT) transmits a broadcast signal to the mobile terminals 100 operating within the system. The broadcast receiving module 111 of FIG. 1 is typically configured inside the mobile terminal 100 to receive broadcast signals transmitted by the BT.

Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites.

Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module.

The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server. The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database.

A method for extracting (analyzing) location information of the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter.

In addition to these position location methods, various algorithms may be used to extract (analyze) location information of a mobile terminal. Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

As previously described with regard to FIG. 1, the mobile terminal may be configured to include short-range communication techniques such as Bluetooth™, Radio Frequency Identification (RFID), Infrared Data Association (IrDA), UltraWideband (UWB), ZigBee, Near Field Communication (NFC), Wireless USB (Wireless Universal Serial Bus), and the like.

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium such as Universal Integrated Circuit Card (UICC) (e.g., a Subscriber Identification Module (SIM) or Universal SIM (USIM)), a secure micro SD and a sticker, or a logical medium (e.g., embedded Secure Element (SE)) embedded in the mobile terminal. Single Wire Protocol (SWP)-based data exchange may be performed between the NFC module and the security module.

In a case where the NFC module operates in a card mode, the mobile terminal may transmit card information on a general IC card to the outside. More specifically, if a mobile terminal having card information on a payment card (e.g., a credit card or a bus card) approaches a card reader, a short-range mobile payment may be executed. As another example, if a mobile terminal which stores card information on an entrance card approaches an entrance card reader, an entrance approval procedure may start. A card such as a credit card, a traffic card, or an entrance card may be included in the security module in the form of applet, and the security module may store card information on the card mounted therein. Card information for a payment card may include any of a card number, a remaining amount and usage history, and the like. Card information of an entrance card may include any of a user's name, a user's number (e.g., undergraduate number or staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs) such as smart poster, text, Uniform Resource Identifier (URI), and general control. If the data received from the external tag is a smart poster type, the controller may execute a browser (e.g., Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in a P2P (Peer-to-Peer) mode, the mobile terminal can execute P2P communication with another mobile terminal. In this case, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For a typical P2P communication, data such as an electronic type name card, address information, a digital photo and a URL, a setup parameter for Bluetooth connection, Wi-Fi connection, etc. may be switched. The P2P mode can be effectively utilized in switching data of a small capacity, because an available distance for NFC communication is relatively short.

Further preferred embodiments will be described in more detail with reference to additional drawing figures. It is understood by those skilled in the art that the present features can be embodied in several forms without departing from the characteristics thereof.

Next, a beauty device 200 in accordance with an embodiment of the present disclosure will be described with reference to FIGS. 2 and 3.

FIG. 2 is a diagram of a beauty device in accordance with an embodiment of the present invention.

The beauty device may refer to a device that is capable of measuring a skin condition of a user or providing a skin care function. Also, the skin care function may include at least one of pore tightening, moisture supply, peeling, ultrasonic stimulation, high-frequency stimulation, and cleansing. Next, the appearance of the beauty device will be described. FIG. 2A illustrates an example of a front appearance and a rear appearance of the beauty device 200, and FIG. 2B illustrates an example of a side appearance of the beauty device 200. As illustrated in FIG. 2A, a measurement unit may be arranged on a front surface of the beauty device 200, and a care unit may be arranged on a rear surface of the beauty device 200. In contrast, the care unit may be arranged on the front surface of the beauty device 200, and the measurement unit may be arranged on the rear surface of the beauty device 200. Also, a care level adjustment button may be provided on the front surface or the rear surface of the beauty device 200. In the present disclosure, a care level is shown as being settable to one of first to fifth levels, but is not limited thereto.

Figure 3:
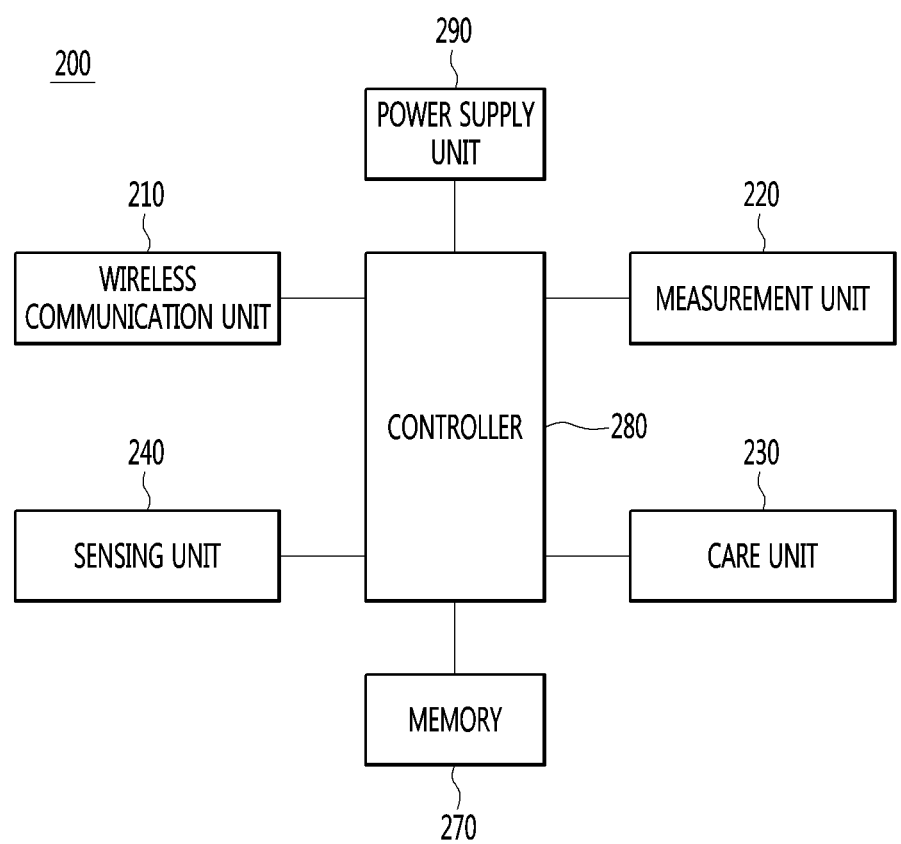
FIG. 3 is a block diagram illustrating a configuration of a beauty device in accordance with an embodiment of the present disclosure.

FIG. 3 is a block diagram illustrating the configuration of the beauty device in accordance with the embodiment of the present disclosure.

In accordance with the embodiment of the present disclosure, the beauty device 200 may include a wireless communication unit 210, a measurement unit 220, a care unit 230, a sensing unit 240, a memory 270, a controller 280, and a power supply unit 290. Also, some of the above-mentioned components may be omitted from the beauty device 200, or the beauty device 200 may further include other components.

The above-described components will be described in more detail. The wireless communication unit 210 may be configured to transmit data to a mobile terminal 100 and receive data from the mobile terminal 100. Specifically, the wireless communication unit 210 may transmit location information of the beauty device 200 to the mobile terminal 100. For example, the wireless communication unit 210 may transmit, to the mobile terminal 100, the location information of the beauty device 200 indicating whether the beauty device 200 is located at a cheek part, corners of eyes, or a forehead. The location information of the beauty device 200 may include a curvature value of a face part at which the beauty device 200 is located, and movement information of the beauty device that is measured by a 9-axis sensor.

The measurement unit 220 may measure a skin condition of a user. Specifically, the measurement unit 220 may measure a moisture and an oil in a touched region. Also, the measurement unit 220 may measure the degree of elasticity and the degree of wrinkle in the touched region. Furthermore, the measurement unit 220 may determine a skin tone of the touched region and measure a pore of the touched region.

The controller 280 may calculate a score of each facial part and a total score by using at least one of the moisture, the oil, the degree of elasticity, the degree of wrinkle, the skin tone, and the pore, which are measured by the measurement unit 220. Also, the controller 280 may determine a skin type and a skin age by using the measurement results of the measurement unit 220.

The care unit 230 may perform a care operation on a skin of the touched region. The care may include at least one of a function of reducing a size of a pore existing in a skin, a function of supplying moisture, a peeling function of guiding granulation by removing an outer layer of a skin, an ultrasonic stimulation function, a high-frequency stimulation function, and a cleansing function.

The sensing unit 240 may determine which part of the face the beauty device 200 touches. To this end, the sensing unit 240 may include a curvature measurer (not shown) and a 9-axis sensor (not shown). First, the curvature measurer will be described below. The curvature measurer may measure a curvature of the touched region. The curvature refers to a variation indicating the degree of curving of a line or a surface. When a point P on a curved line moves at a constant speed along the curved line, a moving direction thereof changes according to a moving distance (length of an arc of the curved line)s. The variation at this time refers to the curvature of the curved line.

The memory 270 may store curvature ranges of parts of the face in association with each other. Therefore, the controller 280 may measure a curvature value of a specific part of the face and acquire a curvature range including the measured curvature value from the memory 270. The controller 280 may recognize the part of the face corresponding to the acquired curvature range as the part of the face at which the beauty device 200 is located. In this manner, the beauty device 200 in accordance with the embodiment of the present disclosure may pre-store the curvature range of each part of the face in the memory 270 by using the fact that people have similar skull shapes, and may determine to which part of the face the measured region corresponds by measuring the curvature value whenever necessary. The case where the beauty device 200 stores the curvature value of each part of the face and determines the part of the face by using the curvature value measured by the beauty device 200 has been described above, but the mobile terminal 100 may store the curvature part of each part of the face, receive the curvature value measured by the beauty device 200, and determine the part of the face based on the received curvature value.

The 9-axis sensor may measure the movement of the beauty device 200. The 9-axis sensor may include an acceleration sensor configured to measure accelerations of x-axis, y-axis, and z-axis directions that include acceleration of gravity, an inertial sensor configured to measure an angular velocity indicating a rotating angle per hour, and a geomagnetic sensor configured to measure an absolute direction by using an earth magnetic field. Therefore, the 9-axis sensor may acquire movement information including the moving direction and the moving distance of the beauty device 200, that is, the direction in which the beauty device 200 moves from the part of the face recognized through the curvature measurer and the distance that the beauty device 200 moves from the part of the face. The controller 280 may track the movement of the beauty device 200 in real time based on the acquired movement information.

The memory 270 may store a skin condition of a user, an average curvature range of each part of the face of people, a measurement and care history, user information, and the like. Also, instead of the memory 270 of the beauty device 200, the memory 170 of the mobile terminal 100 may store some pieces of the above-mentioned information. Alternatively, the beauty device 200 and the mobile terminal 100 may store the pieces of the above-mentioned information separately according to a memory capacity.

The controller 280 may control operations of the respective components included in the beauty device 200.

The power supply unit 290 may receive external power and internal power and supply power necessary for the operations of the respective components. The power supply unit 290 may include a battery, and the battery may be a rechargeable internal battery, or may be detachably connected to a terminal body for the purpose of charging or the like. Furthermore, the power supply unit 290 may include a connection port. The connection port may be configured such that an external charger for supplying power to recharge the battery is electrically connected thereto.

Next, a skin measurement algorithm in accordance with an embodiment of the present disclosure will be described with reference to FIG. 4.

Figure 4:
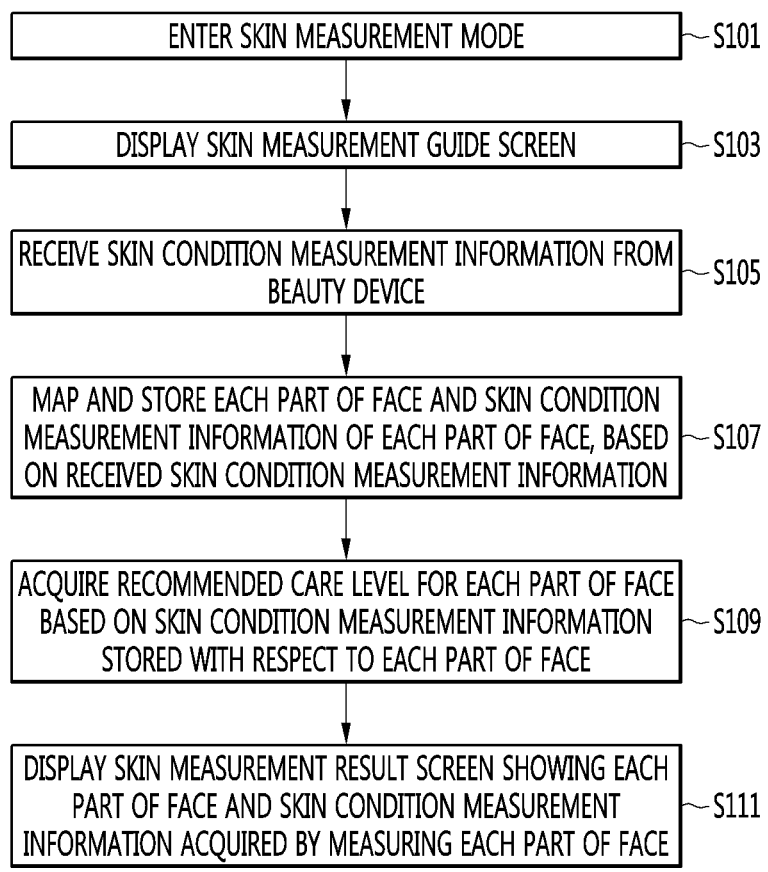
FIG. 4 is a flowchart of a skin measurement algorithm in accordance with an embodiment of the present invention.

FIG. 4 is a flowchart of a skin measurement algorithm in accordance with an embodiment of the present invention.

The controller 180 may enter a skin measurement mode (S101). The beauty device 200 in accordance with the embodiment of the present disclosure may provide only a skin measurement function. The beauty device 200 in accordance with another embodiment of the present disclosure may provide only a skin care function. The beauty device 200 in accordance with further another embodiment of the present disclosure may provide both the skin measurement function and the skin care function. Hereinafter, the beauty device 200 that provides both the skin measurement function and the skin care function will be described by way of example.

When the controller 180 enters the skin measurement mode, a skin measurement control signal may be transmitted to the beauty device 200. When the beauty device 200 receives the skin measurement control signal, the beauty device 200 may operate in a skin condition measurement mode.

Then, the controller 180 may display a skin measurement guide screen (S103). The controller 180 may display the skin measurement guide screen showing a measuring sequence of parts of a face, so as to measure a skin condition with respect to each part of the face.

Next, the skin measurement guide screen in accordance with an embodiment of the present disclosure will be described with reference to FIGS. 5 to 8.

FIGS. 5 to 8 are diagrams for describing the skin measurement guide screen in accordance with an embodiment of the present disclosure.

Figure 5:
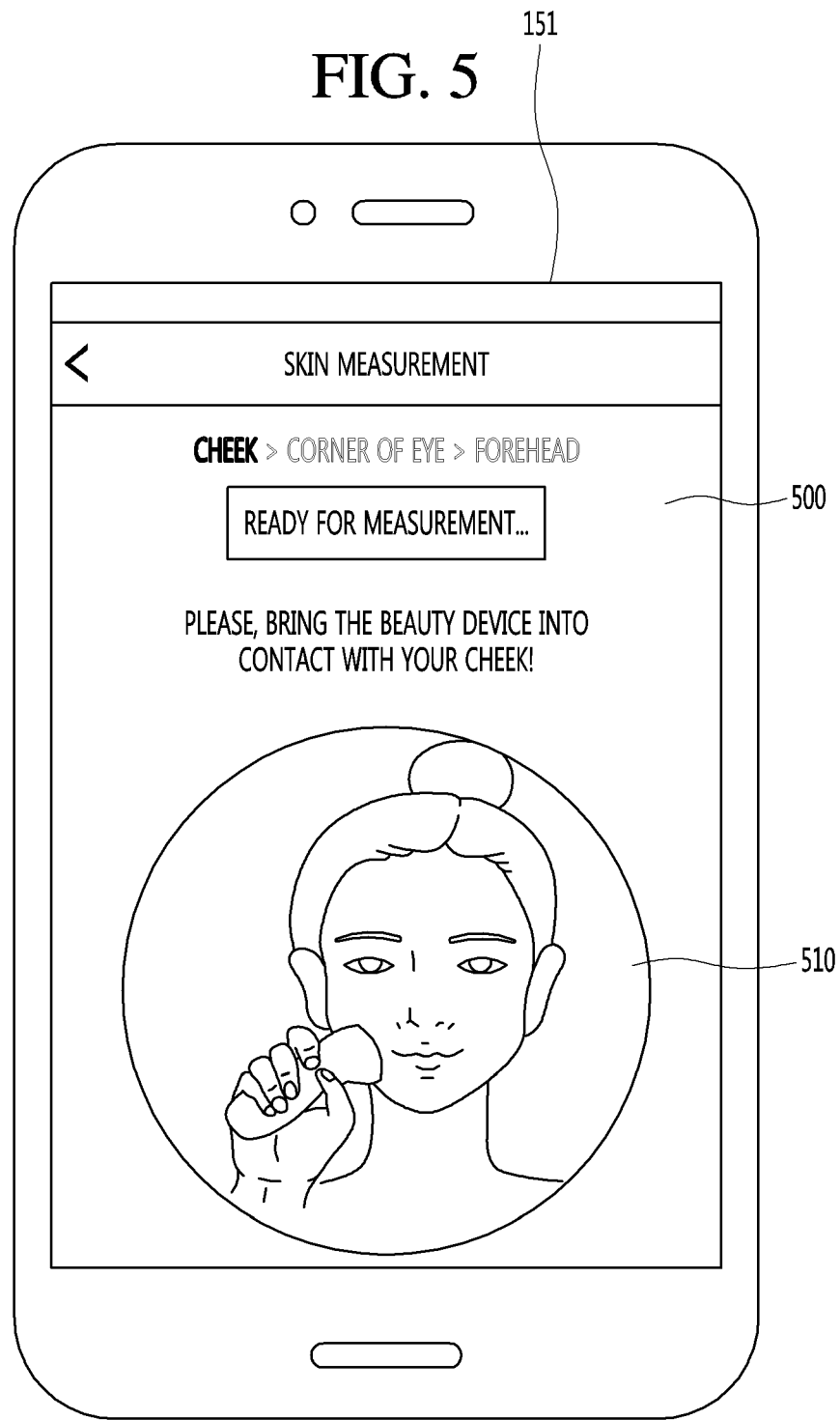
FIGS. 5 to 8 are diagrams for describing a skin measurement guide screen in accordance with an embodiment of the present disclosure.

As illustrated in FIG. 5, the display unit 151 may display the skin measurement guide screen 500. The skin measurement guide screen 500 may include at least one of a measuring sequence of parts of a face, a state of the beauty device 200, a guide message, and a guide image 510.

First, the measuring sequence will be described below. The measuring sequence is provided for storing the measurement results while mapping the parts of the face. The skin measurement guide screen 500 in accordance with the present disclosure guides the skin measurement in the sequence of a cheek, corners of eyes, and a forehead, but this is merely an example.

The state of the beauty device 200 indicates a state prior to the skin condition measurement, a state in which the skin condition measurement is being performed, or a state in which the skin condition measurement has been completed. A user may confirm from the state of the beauty device 200 whether the skin condition measurement is exactly performed.

Figure 6:
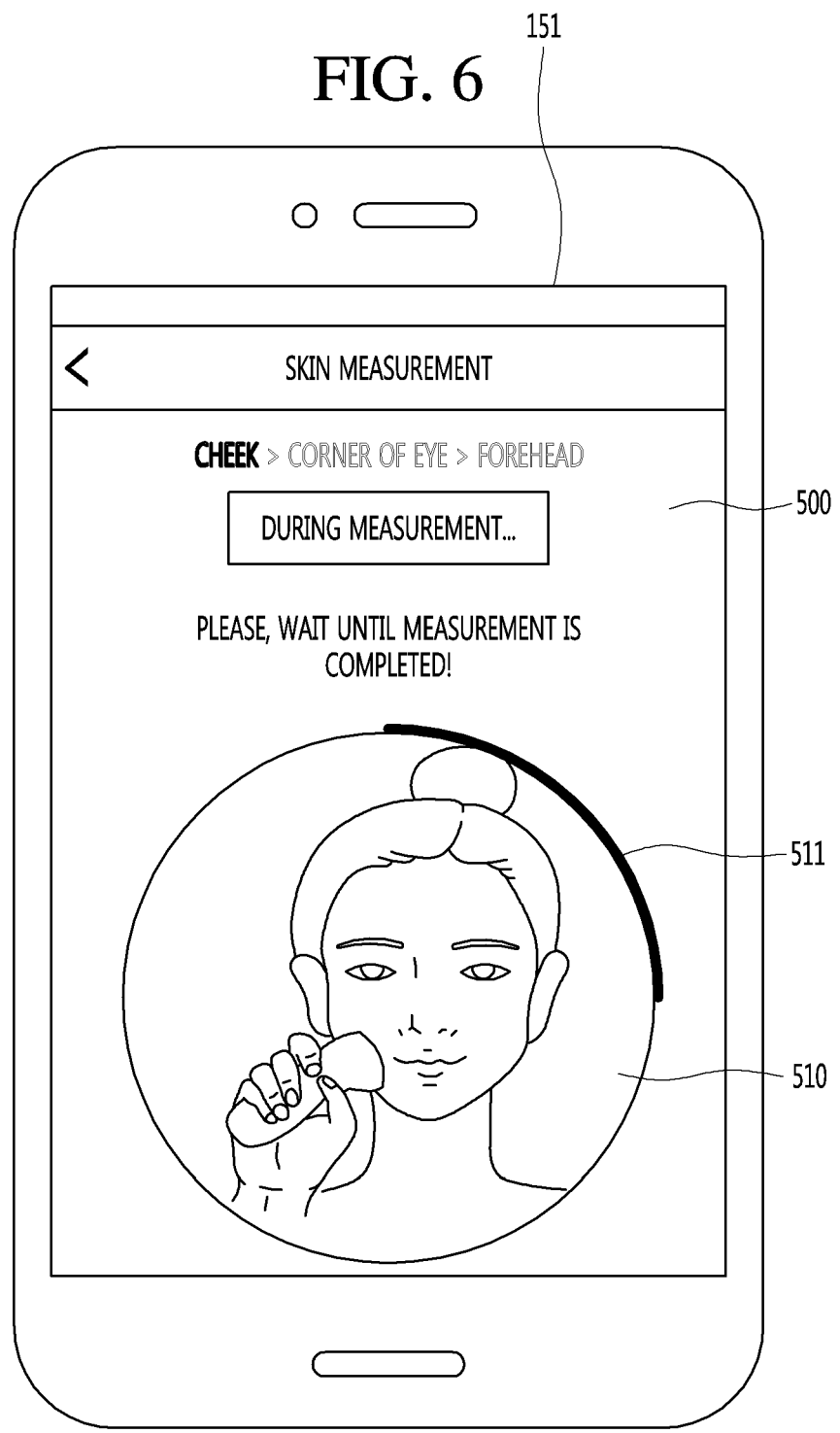
Figure 7:
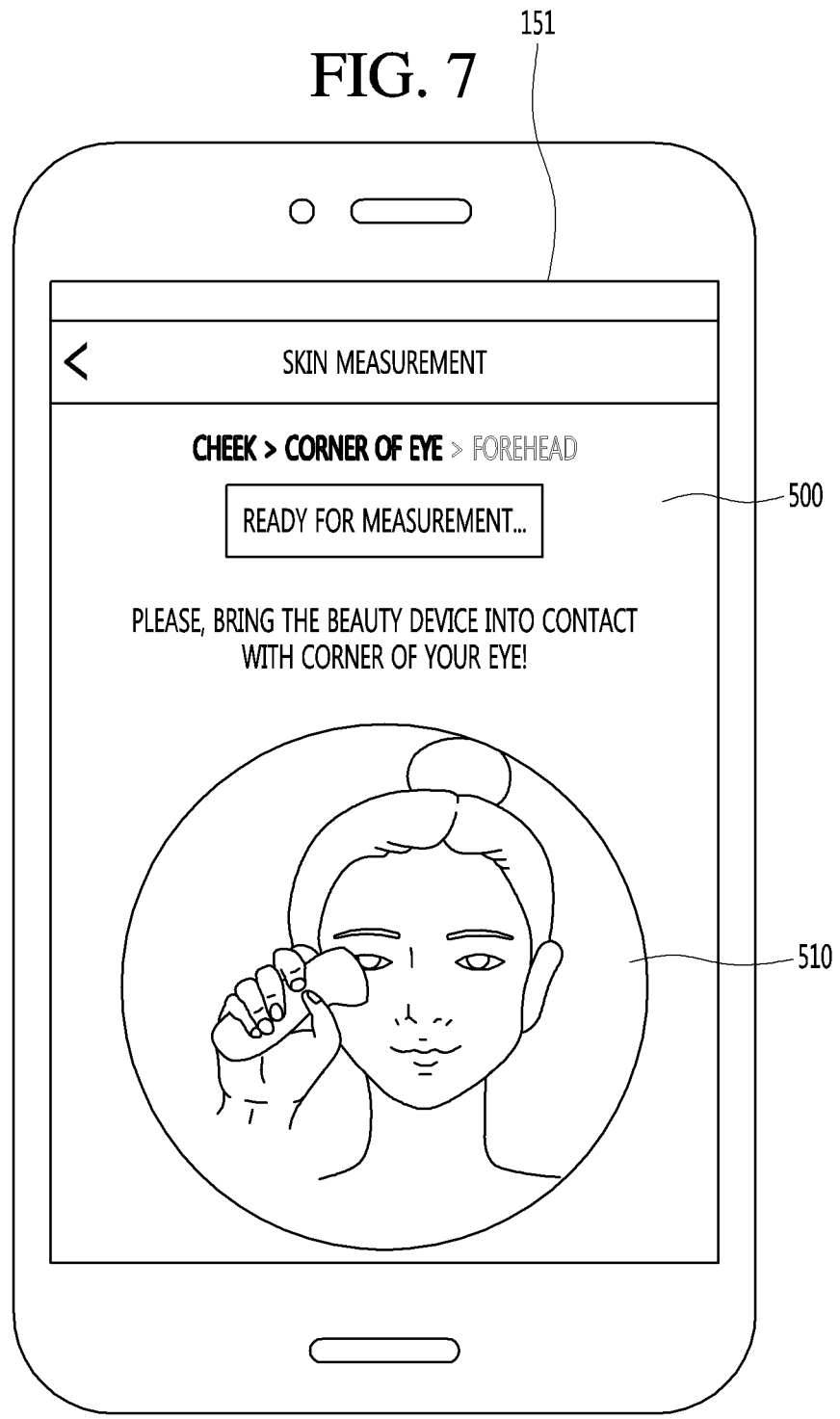
Figure 8:
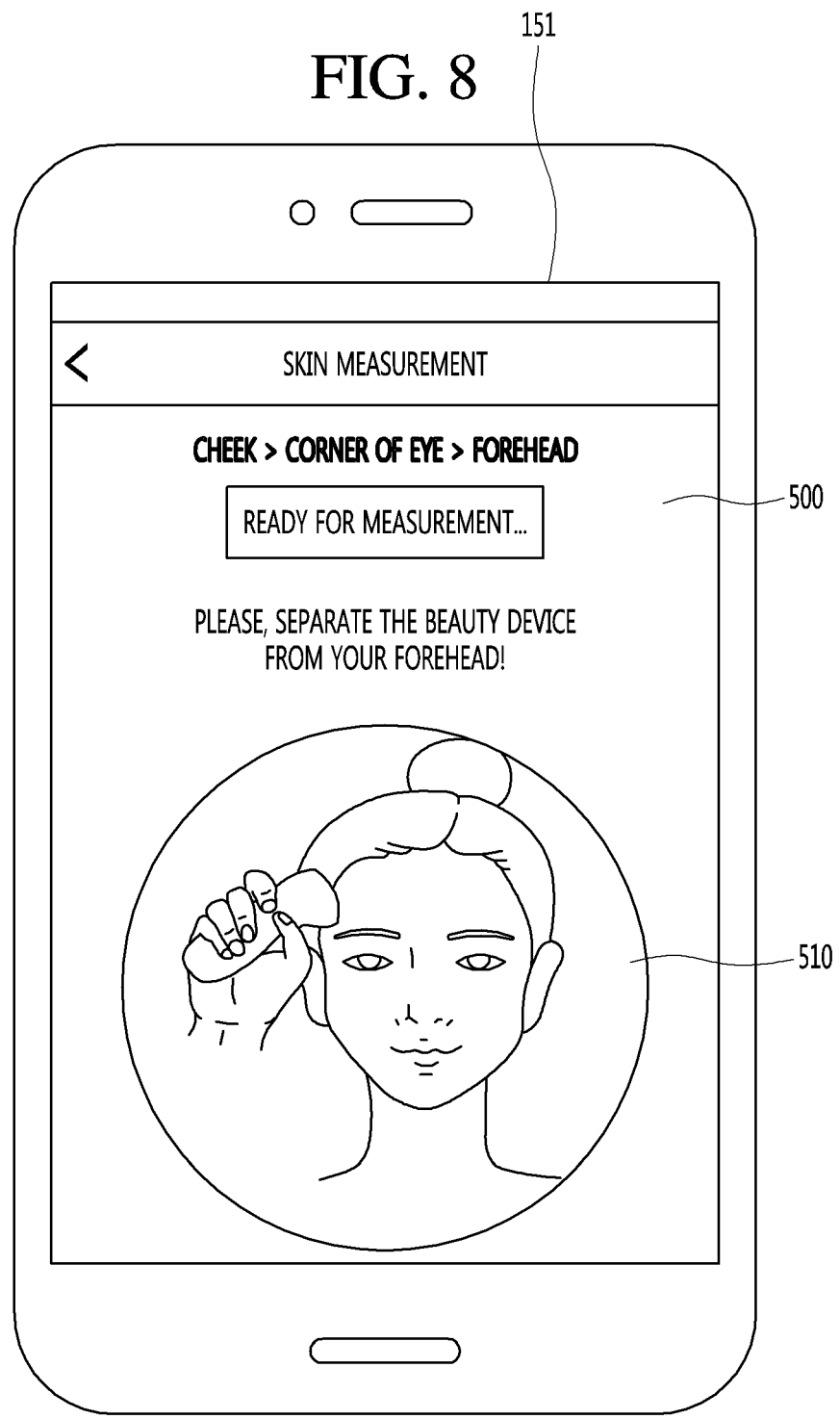

Then, the guide message may display an instruction for the skin condition measurement. For example, the guide message may display an instruction "Please, bring the beauty device into contact with your cheek!" as illustrated in FIG. 5, an instruction "Please, wait until measurement is completed!" as illustrated in FIG. 6, an instruction "Please, bring the beauty device into contact with corner of your eye!" as illustrated in FIG. 7, or an instruction "Please, separate the beauty device from your forehead!" as illustrated in FIG. 8. The user can see the information displayed in the guide message and know how the user moves the beauty device 200.

The guide image 510 may mean an image represented by a still picture or a moving picture so as to make it easier for the user to understand information similar to the guide message. The user can easily confirm the skin condition measurement method by following what the guide image 510 displays.

The skin measurement guide screen 500 of FIG. 5 is a stage for measuring a current skin condition of a cheek and indicates a measurement standby state that is prior to the start of the measurement. Also, the skin measurement guide screen 500 of FIG. 5 guides the user to bring the beauty device 200 into contact with the user's cheek. The skin measurement guide screen 600 of FIG. 6 is a stage in which the skin condition of the cheek is being measured, and guides the user to maintain a current state until the measurement is completed. The display unit 151 may further display a time guide 511 so as to notify the user of how long the user has to maintain the current state. In the present disclosure, the time guide 511 may progress clockwise in a shape of a circle surrounding the periphery of the guide image 510. When the time guide 511 completely surrounds the periphery of the guide image 510 in the shape of the circle, it may mean the completion of the skin condition measurement. The skin measurement guide screen 500 of FIG. 7 is a stage for measuring a current skin condition of the corners of eyes, and guides the user to bring the beauty device 200 to the corners of eyes in the current measurement standby state. The skin measurement guide screen 500 of FIG. 8 guides the user to separate the beauty device 200 from the skin because the skin measurements of the cheek, the corners of eyes, and the forehead are completed.

Referring again to FIG. 4, the wireless communication unit 110 may receive skin condition measurement information from the beauty device 200 (S105).

The wireless communication unit 110 may receive, from the beauty device 200, skin condition measurement information acquired by measuring each part of the face through the beauty device 200.

The controller 180 may map and store each part of the face and the skin condition measurement information of each part of the face in the memory 170, based on the received skin condition measurement information (S107).

The controller 180 may map and store each part of the face, which is measured in sequence through the skin measurement guide screen 500, and the skin condition measurement information of each part of the face in the memory 170. For example, the controller 180 may perform control to map and store, in the memory 170, the cheek part of the face and the skin condition measurement information measured when the skin measurement guide screen 500 guides the cheek, to map and store, in the memory 170, the corner of eye and the skin condition measurement information measured when the skin measurement guide screen 500 guides the corner of eye, and to map and store, in the memory 170, the forehead part of the face and the skin condition measurement information measured when the skin measurement guide screen 500 guides the forehead.

The controller 180 may acquire a recommended care level for each part of the face based on the skin condition measurement information stored with respect to each part of the face (S109).

The controller 180 may set a recommended care level for each part of the face based on the skin condition measurement information of each part of the face. For example, the controller 180 may set the care level to be low when the skin condition of the cheek is good, and may set the care level to be high when the skin condition of the forehead is bad. When the skin condition measurement information is different with respect to each part of the face, the recommended care level may be differently set with respect to each part of the face.

Also, the controller 180 may determine the recommended care level for each part of the face by reflecting general feature information on each part of the face. For example, since the skin around the eyes is weaker than the cheek or the forehead, the controller 180 may set the recommended care level to be 3 or less.

The recommended care level for each part of the face, which is set in the above-described manner, may be used when the beauty device 200 operates in the skin care mode.

The controller 180 may display a skin measurement result screen showing each part of the face and the skin condition measurement information acquired by measuring each part of the face (S111).

The skin measurement result screen 900 may be a screen for notifying the user of the skin condition of each part of the face.

Figure 9:
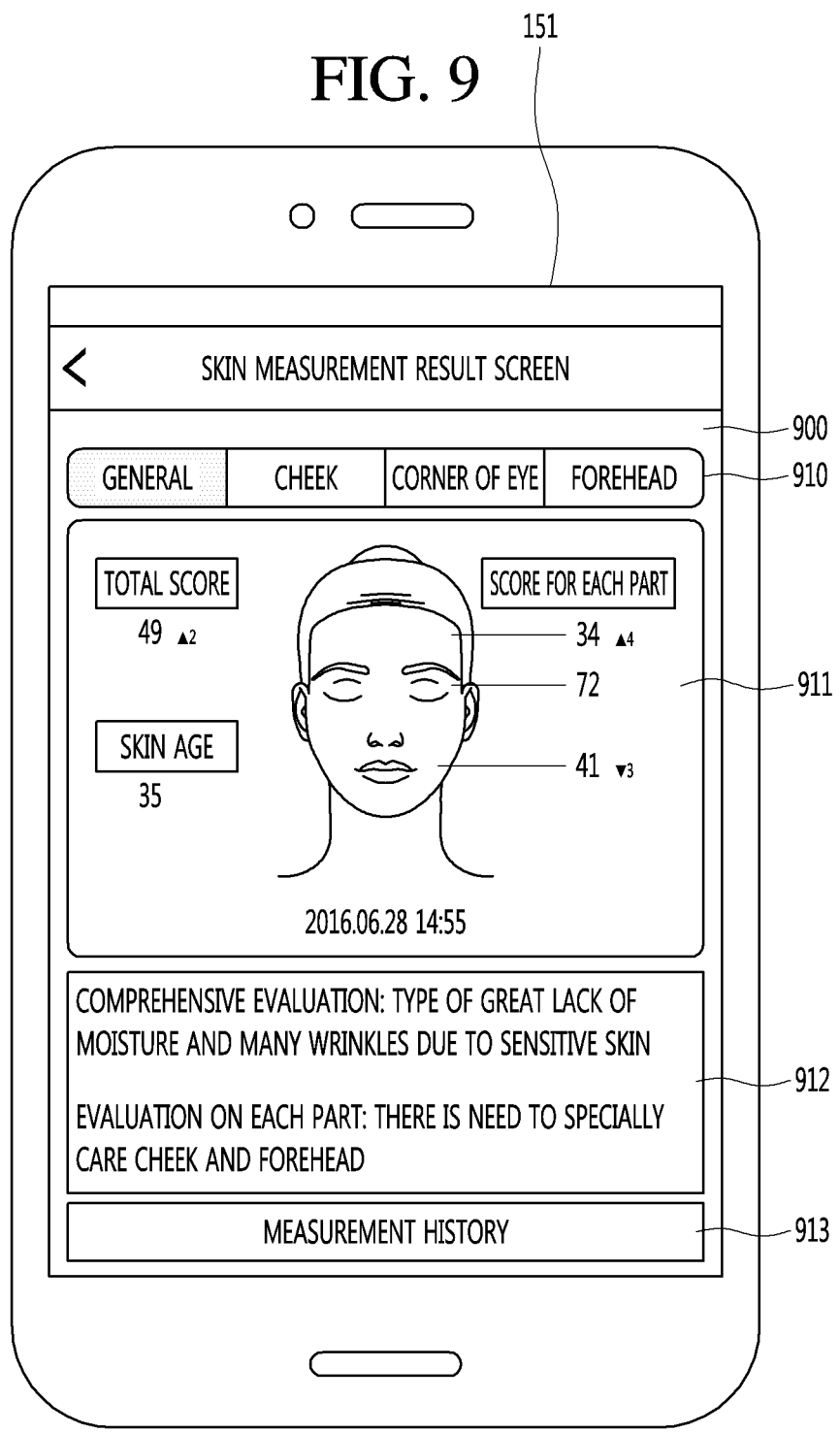
FIGS. 9 to 10 are diagrams for describing a skin measurement result screen in accordance with an embodiment of the present disclosure.

Next, the skin measurement result screen in accordance with an embodiment of the present disclosure will be described with reference to FIGS. 9 and 10.

The skin measurement result screen 900 may include a skin measurement result screen for an entire face and a skin measurement result screen for each part of the face. The skin measurement result screen 900 illustrated in FIG. 9 may be the skin measurement result screen related to the entire face. The skin measurement result screen 900 illustrated in FIG. 9 may include a skin score 911, a skin evaluation 912, and a measurement history icon 913.

The skin score 911 may include a score of each part of the face, i.e., the cheek, the corner of eye, the forehead, a total score calculated by totaling the score of each part of the face, and a skin age based on the total score. As such, by expressing the skin measurement result with a numerical value, the user can easily feel the skin condition and the change in the skin condition.

The skin evaluation 912 may include a current skin condition of the entire face and a skin condition requiring a care with respect to each part of the face. Also, the skin evaluation 912 may include a comparison evaluation with respect to a previous skin condition measurement result.

The measurement history icon 913 is an icon for comparison with the previous skin condition measurement result.

Figure 10:
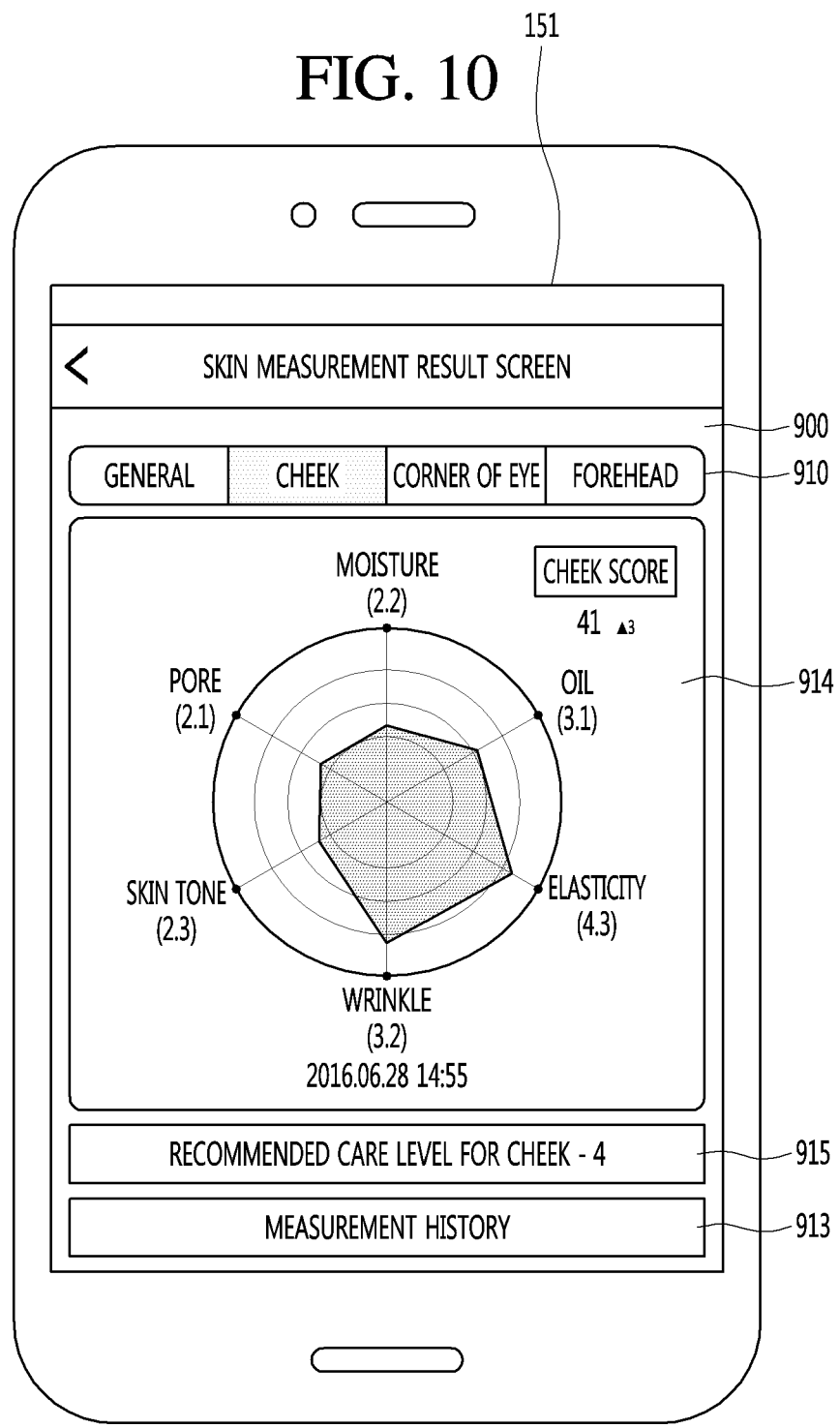

The skin measurement result screen 900 illustrated in FIG. 10 may be the skin measurement result screen related to each part of the face. The skin measurement result screen 900 illustrated in FIG. 10 may include scores obtained by calculating a moisture, an oil, a degree of elasticity, a degree of wrinkle, a skin tone, and pores with respect to each part of the face. Therefore, the user can confirm a care specially required in relation to the corresponding part of the face through the skin measurement result screen 900 for each part of the face. Also, the skin measurement result screen 900 may include a recommended care level for each part of the face. Through the recommended care level, it is possible to solve a problem that it is difficult for the user to directly determine which care level is required with respect to each part of the face. The measurement history icon 913 included in the skin measurement result screen 900 for each part of the face as illustrated in FIG. 10 is an icon for confirming the records of the moisture, the oil, the degree of elasticity, the degree of wrinkle, the skin tone, and the pores, which have been previously measured with respect to each part of the face.

Next, a skin care algorithm in accordance with an embodiment of the present disclosure will be described with reference to FIG. 11.

Figure 11:
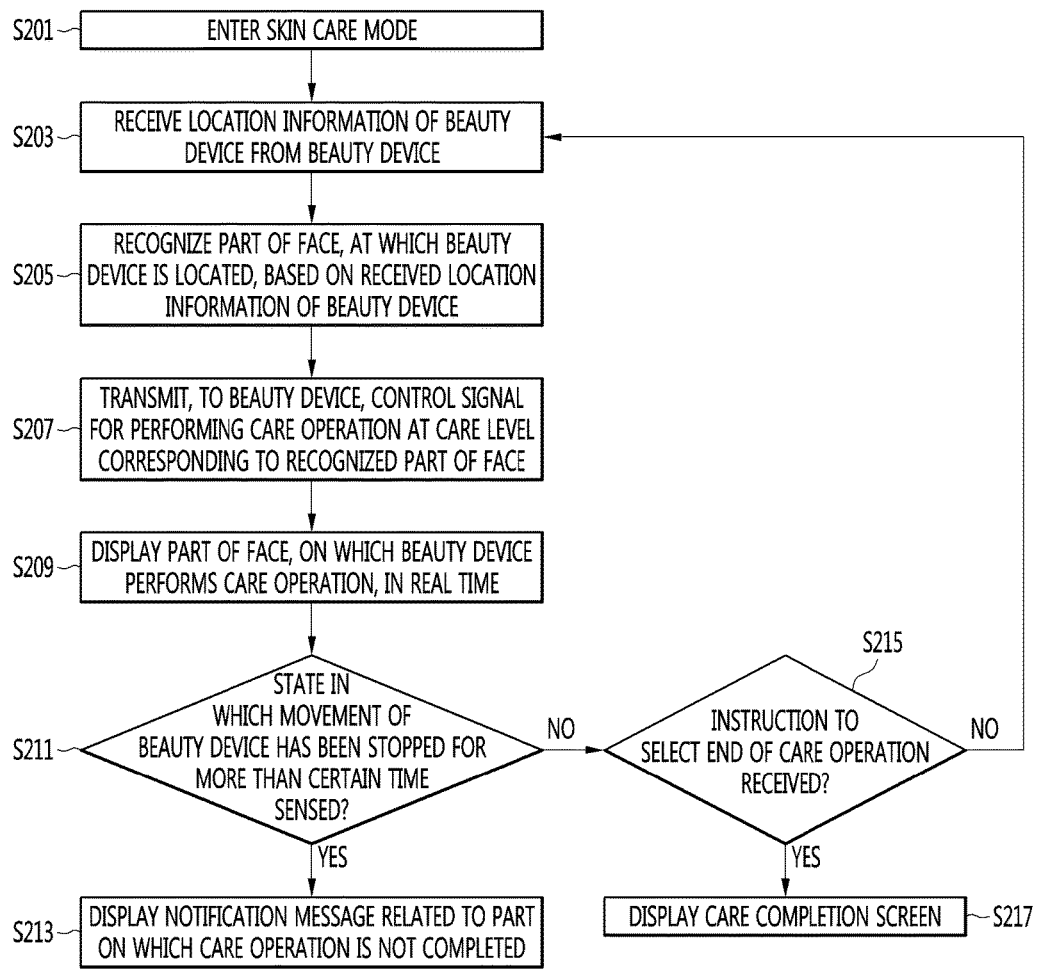
FIG. 11 is a flowchart of a skin care algorithm in accordance with an embodiment of the present invention.

FIG. 11 is a flowchart of a skin care algorithm in accordance with an embodiment of the present invention.

The controller 180 may enter a skin care mode (S201). When the controller 180 enters the skin care mode, a skin care control signal may be transmitted to the beauty device 200.

The controller 180 may receive location information of the beauty device 200 from the beauty device 200 (S203). The location information of the beauty device 200 that the controller 180 receives from the beauty device 200 may include a curvature and movement information of a region touched by the beauty device 200. The curvature of the region touched by the beauty device 200 may be acquired by the curvature measurer included in the sensing unit 240 of the beauty device 200. The movement information of the region touched by the beauty device 200 may be acquired by the 9-axis sensor included in the sensing unit 240 of the beauty device 200.

The controller 180 may recognize the part of the face, at which the beauty device 200 is located, based on the received location information of the beauty device 200 (S205).

In accordance with the embodiment of the present disclosure, the controller 180 may receive the location information of the beauty device 200 and acquire the part of the face, at which the beauty device 200 is located. First, the controller 180 may determine which part of the face the region is touched by the beauty device 200, based on the curvature information of the region touched by the beauty device 200. Specifically, the memory 170 may store a curvature range of each part of the face. For example, the memory 170 may store 40R to 60R as the curvature range of the cheek, 30R to 40R as the curvature range of the corner of eye, and 10R to 30R as the curvature range of the forehead. Therefore, when the curvature of the region touched by the beauty device 200 is 50R, the controller 180 may determine that the current location of the beauty device 200 is the cheek corresponding to the curvature range including 50R. Similarly, when the curvature of the region touched by the beauty device 200 is 20R, the controller 180 may determine that the current location of the beauty device 200 is the forehead corresponding to the curvature range including 20R. The above-described curvature range of each part of the face is merely an example and is not limited thereto. Also, the curvature measurement method of the sensing unit 240 included in the beauty device 200 may include methods according to the related art.

The controller 180 may acquire the location of the beauty device 200 based on the movement information acquired by the 9-axis sensor included in the beauty device 200. Specifically, the movement information received from the beauty device 200 may include information indicating a moving direction and a moving distance of the beauty device 200. Therefore, the controller 180 may acquire the part of the face, at which the beauty device 200 is located, by combining the part of the face acquired based on the curvature and the moving direction and the moving distance of the beauty device 200.

In accordance with another embodiment of the present disclosure, the controller 180 may acquire the part of the face, at which the beauty device 200 is located, based on a pattern change. The controller 280 of the beauty device 200 may output an arbitrary pattern to a touched region. The output pattern may be differently changed according to the shape of the touched region. For example, a shape of a pattern output to a forehead part may be little changed, but a shape of a pattern output to a nose part may be greatly distorted. The controller 180 may acquire the part of the face, at which the beauty device 200 is located, based on the degree of change in the shape of the pattern or the changed shape.

In accordance with further another embodiment of the present disclosure, the controller 180 may acquire the part of the face, at which the beauty device 200 is located, based on the received skin condition measurement information. The controller 180 may acquire the part of the face, at which the beauty device 200 is located, by using feature information on each part of the faces of general people. For example, the memory 170 may store information indicating that much oil is present on the foreheads of the general people and pores in the corner of eye are small. Therefore, the controller 180 may recognize the forehead part when the corresponding region has a large amount of oil in the measured skin condition, and may recognize the cheek part when the corresponding region has small pores.

The controller 180 may transmit, to the beauty device 200, a control signal for performing a care operation at a care level corresponding to the recognized part of the face (S207).

The controller 180 may automatically recognize the part of the face and transmit, to the beauty device 200, a control signal for performing a care operation at a care level corresponding to the acquired part of the face. The beauty device 200 may perform the care operation at the care level corresponding to the acquired part, based on the received control signal. The care level corresponding to each part of the face may be acquired by the method described above with reference to S109 of FIG. 4.

When the part of the face, at which the beauty device 200 is located, is changed, the controller 180 may transmit, to the beauty device 200, a control signal for changing the care level according to the change. Therefore, when the part of the face is changed, the beauty device 200 may automatically change the care level according to the change. Hence, even when the user changes the part of the face that is being cared with the beauty device 200, the user can care the face conveniently without manually changing the care level according to the change.

The display unit 151 may display the part of the face, on which the beauty device 200 performs the care operation, in real time (S209). Specifically, the display unit 151 may display the acquired part of the face, at which the beauty device 200 is located, in real time.

Next, a method by which the display unit 151 displays the location of the beauty device 200 will be described with reference to FIGS. 12 to 19.

FIGS. 12 to 19 are diagrams for describing a method by which the display unit displays the part of the face, at which the beauty device is located, in accordance with an embodiment of the present disclosure.

Figure 12:
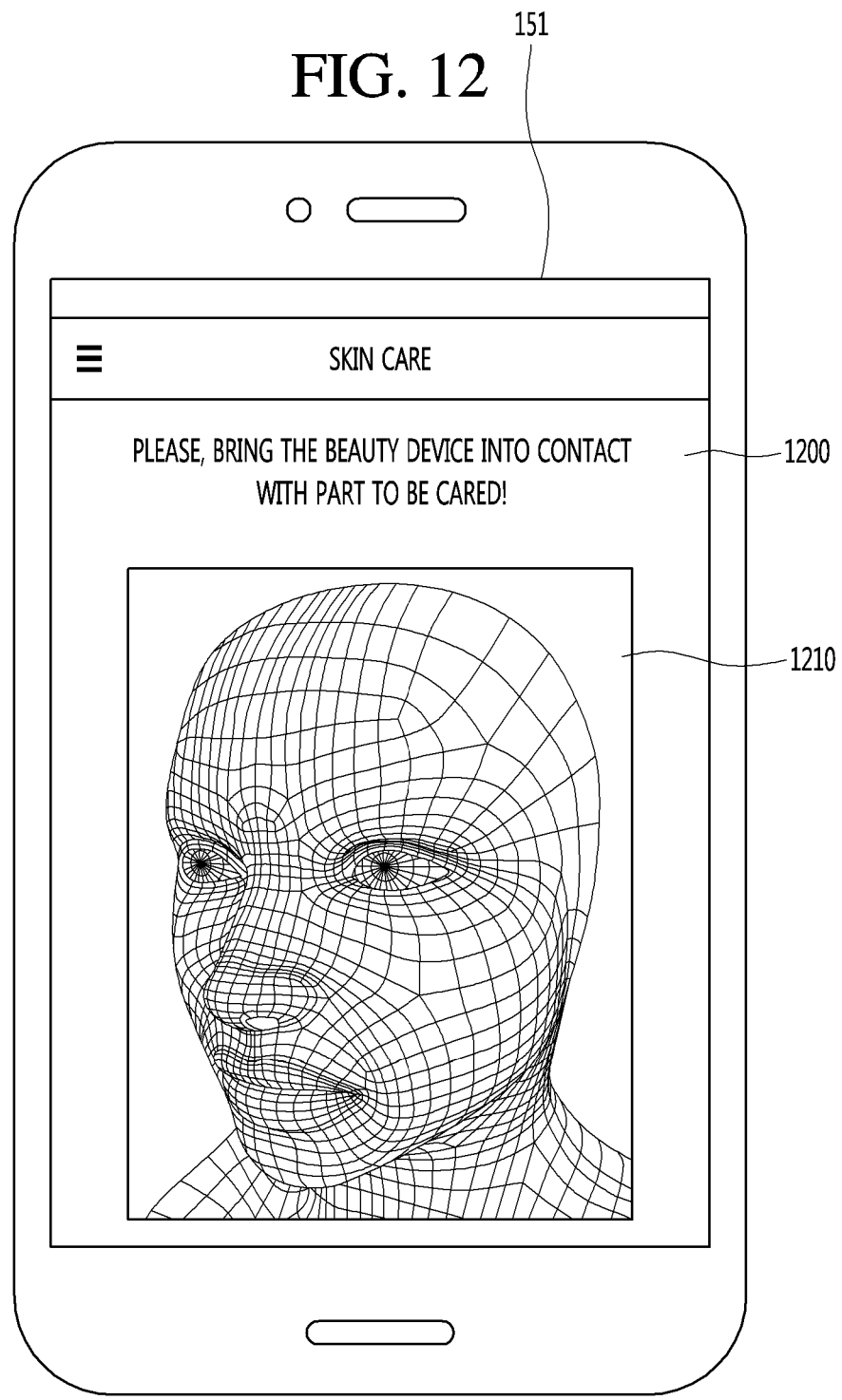
FIGS. 12 to 19 are diagrams for describing a method by which a display unit displays a part of a face, at which a beauty device is located, in accordance with an embodiment of the present disclosure.

As illustrated in FIG. 12, the display unit 151 may display a care tracking screen 1200. The care tracking screen 1200 may include a face simulation 1210. Alternatively, the care tracking screen 1200 may include a user's face photographed by the camera 121, instead of the face simulation 1210. When the controller 180 enters the skin care mode, the display unit 151 may display the care tracking screen 1200 as illustrated in FIG. 12. When the beauty device 200 performs the care operation, the display unit 151 may display the part of the face, at which the beauty device 200 is located, on the care tracking screen 1200. The display unit 151 may display the part of the face, which is recognized in S205 of FIG. 11, on the care tracking screen 1200 in real time. The display unit 151 may display the part of the face, which is being cared by the beauty device 200, on the care tracking screen 1200.

Figure 13:
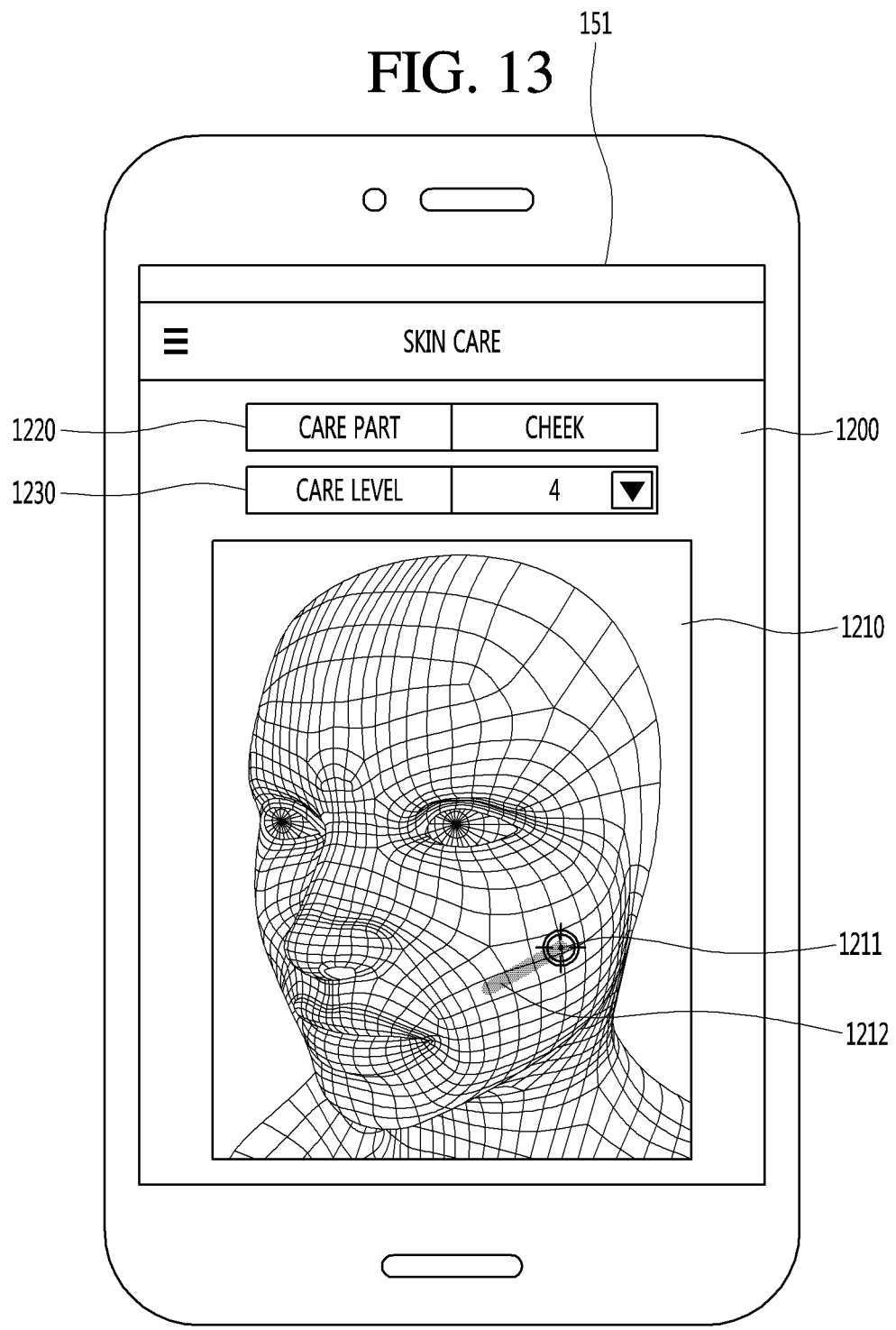

In accordance with the embodiment of the present disclosure, the display unit 151 may display the part of the face, which is being cared, on the care tracking screen 1200 as illustrated in FIG. 13. Specifically, the display unit 151 may display a care location mark 1211 indicating a region being currently cared on the face simulation 1210. Also, the care tracking screen 1200 may further include a care part 1220 indicating which part of the face is being cared. That is, the care tracking screen 1200 may display the part of the face corresponding to the care location mark 1211 in the care part 1220. Also, the care tracking screen 1200 may further include a care level 1230 that is being applied to the care part. When receiving an input of selecting the care level 1230, the controller 180 may change the currently applied care level to another care level. Also, the display unit 151 may display a care progress status mark 1212 indicating a region cared by the beauty device 200 on the face simulation 1210. Also, the display unit 151 may display a care progress status mark 1212 corresponding to a region through which the care location mark 1211 passes. Also, the display unit 151 may display the care progress status mark 1212 with different opacity according to the degree of progress of care or the degree of care required.

Figure 14:
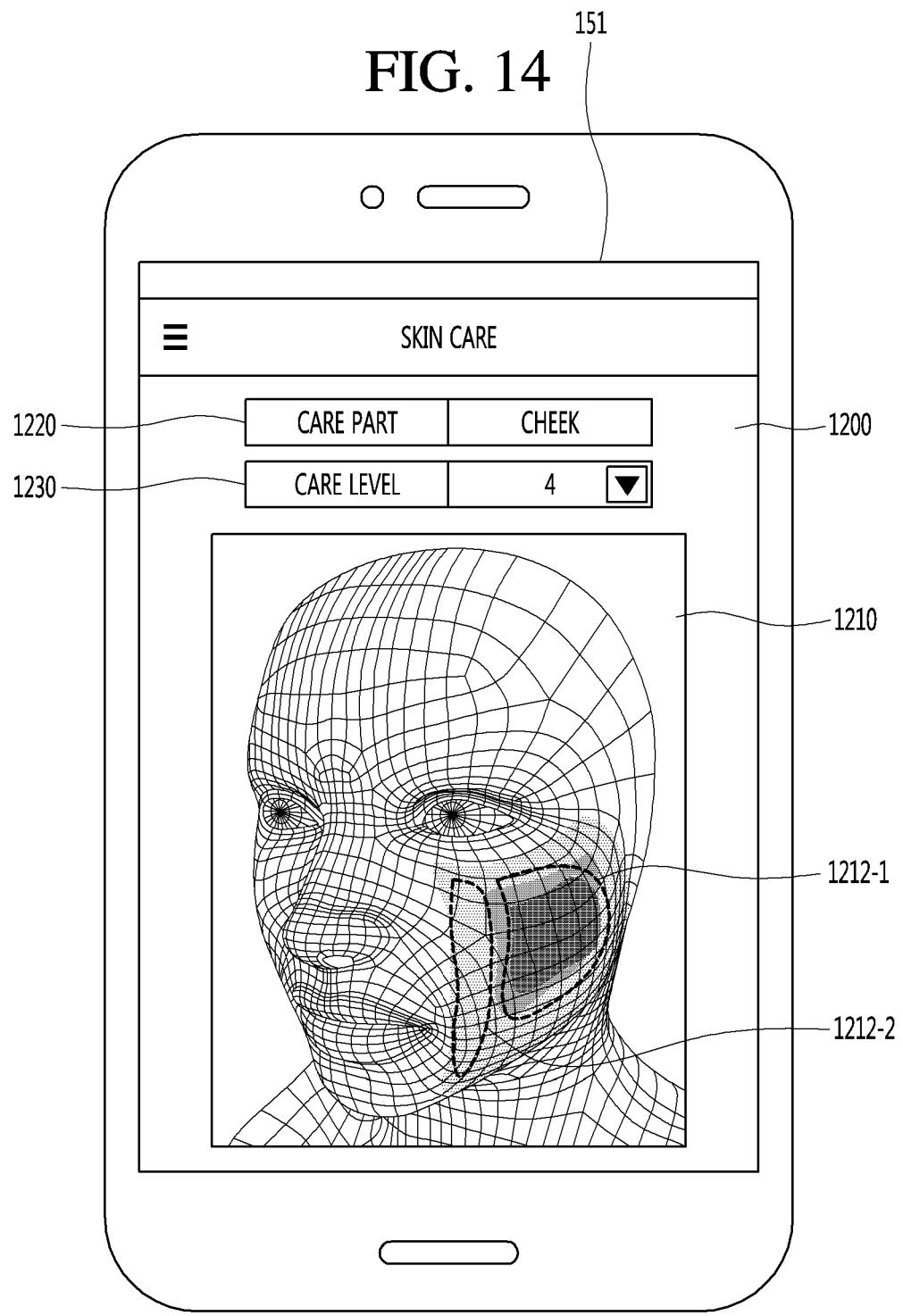

Next, a method of displaying the care progress status mark with different opacity in accordance with an embodiment of the present disclosure will be described. As illustrated in FIG. 14, the display unit 151 may display the care progress status mark 1212 with different opacity. For example, when the beauty device 200 passes many times, the display unit 151 may display the care progress status mark 1212 with dark opacity. In the example of FIG. 14, a first care progress status mark 1212-1 may indicate that the care operation has been performed many times, and a second care progress status mark 1212-2 may indicate that the care operation has been less performed as compared to a region corresponding to the first care progress status mark 1212-1. As another example, the display unit 151 may display the care progress status mark 1212 with different opacity according to the degree of care required. The display unit 151 may display a region requiring high-intensity care with light opacity and may display a region requiring low-intensity care with dark opacity. Therefore, even though the region corresponding to the first care progress status mark 1212-1 and the region corresponding to the second care progress status mark 1212-2 have been cared to the substantially equal degree, the region corresponding to the first care progress status mark 1212-1 is a region requiring lower-intensity care and is displayed darker than the region corresponding to the second care progress status mark 1212-2.

Figure 15:
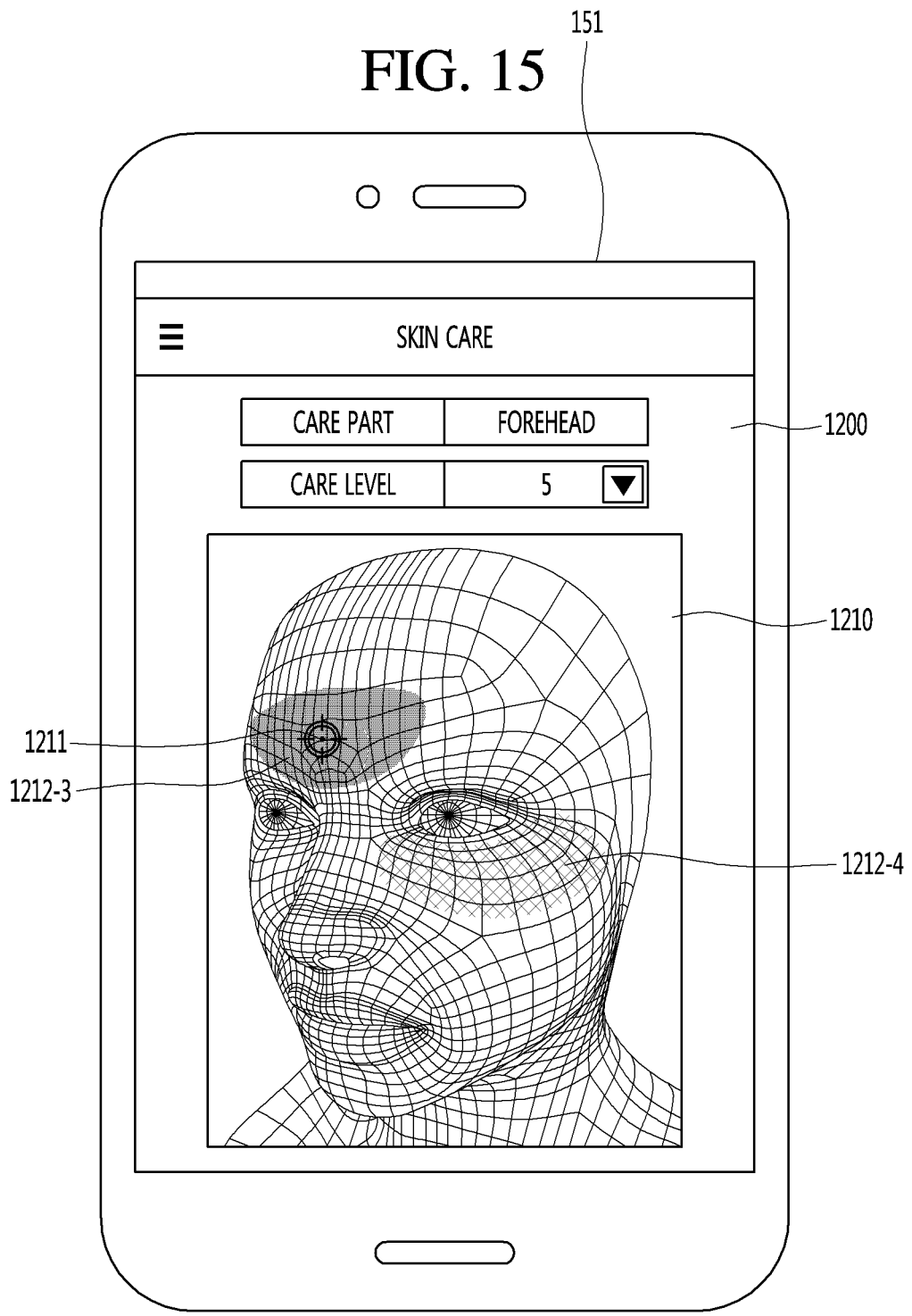

Also, as illustrated in FIG. 15, the display unit 151 may differently display the care progress status mark 1212 according to each part of the face or the care level. For example, a first care progress status mark 1212-3 and a second progress status mark 1212-4 indicate different parts of the face. That is, the first care progress status mark 1212-3 indicates a region corresponding to a forehead, and the second care progress status mark 1212-4 indicates a region corresponding to the corner of eye. Thus, the display unit 151 may display the care progress status mark 1212 in a distinguishably manner.

As another example, the display unit 151 may display the care progress status mark 1212 in a distinguishably manner so as to indicate that the beauty device 200 is operated at a care level 5 in the region corresponding to the first care progress status mark 1212-3 and the beauty device 200 is operated at a care level 4 in the region corresponding to the second care progress status mark 1212-4. In order to discriminating the care progress status mark 1212, the display unit 151 may display the first care progress status mark 1212-3 and the second care progress status mark 1212-4 with different colors.

Figure 16:
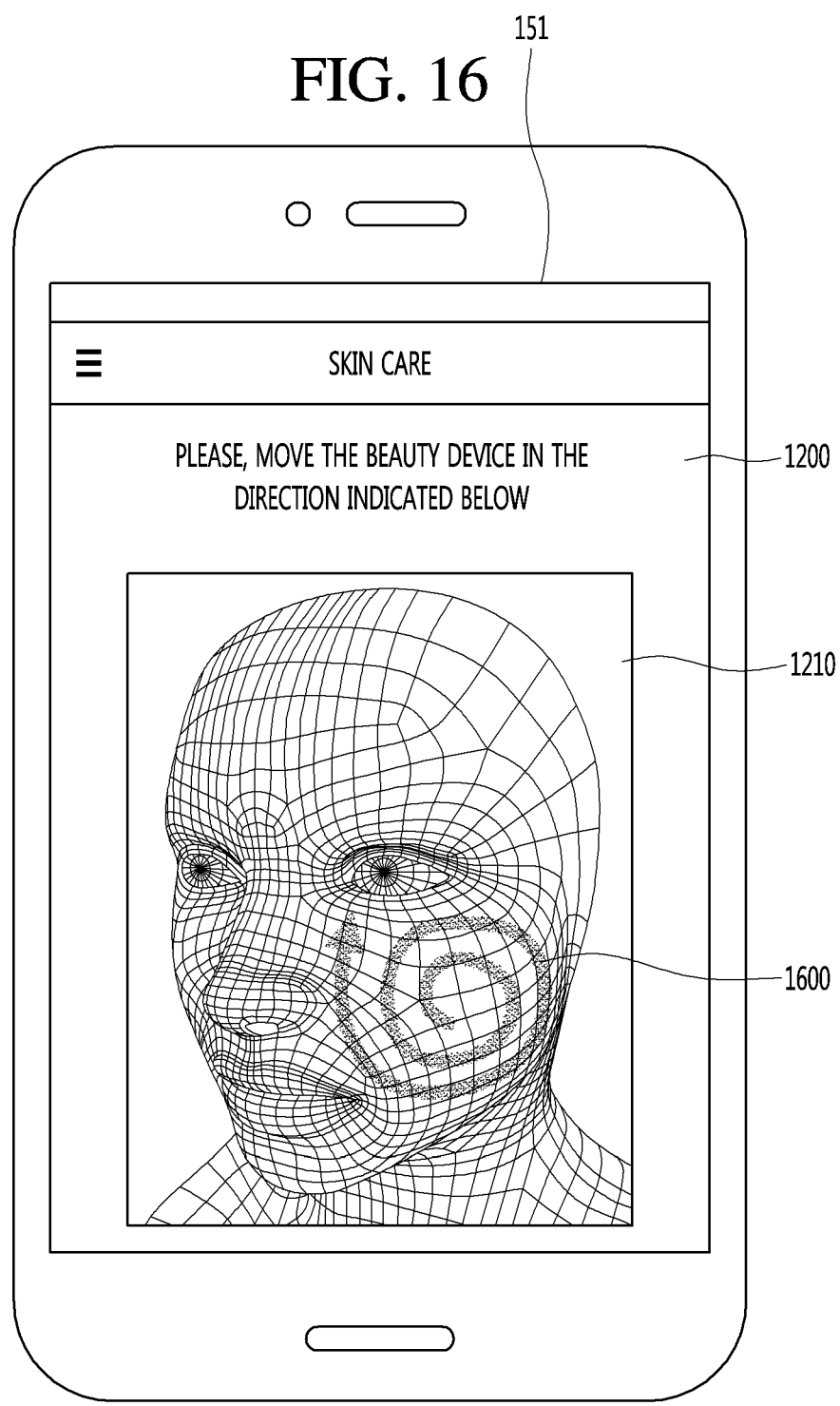

Also, as illustrated in FIG. 16, the display unit 151 may display a care guide line 1600 on the care tracking screen 1200. The care guide line 1600 may indicate a recommended care method for a corresponding region. The care guide line 1600 may be differently set for each part of the face. The care guide line 1600 may be received from other users. For example, the care guide line 1600 may be a recommended care method uploaded to a server by a dermatology or a popular entertainer. As illustrated in FIG. 16, the user may move the beauty device 200 clockwise from the central region to the outer region of the cheek with reference to the care guide line 1600.

Figure 17:
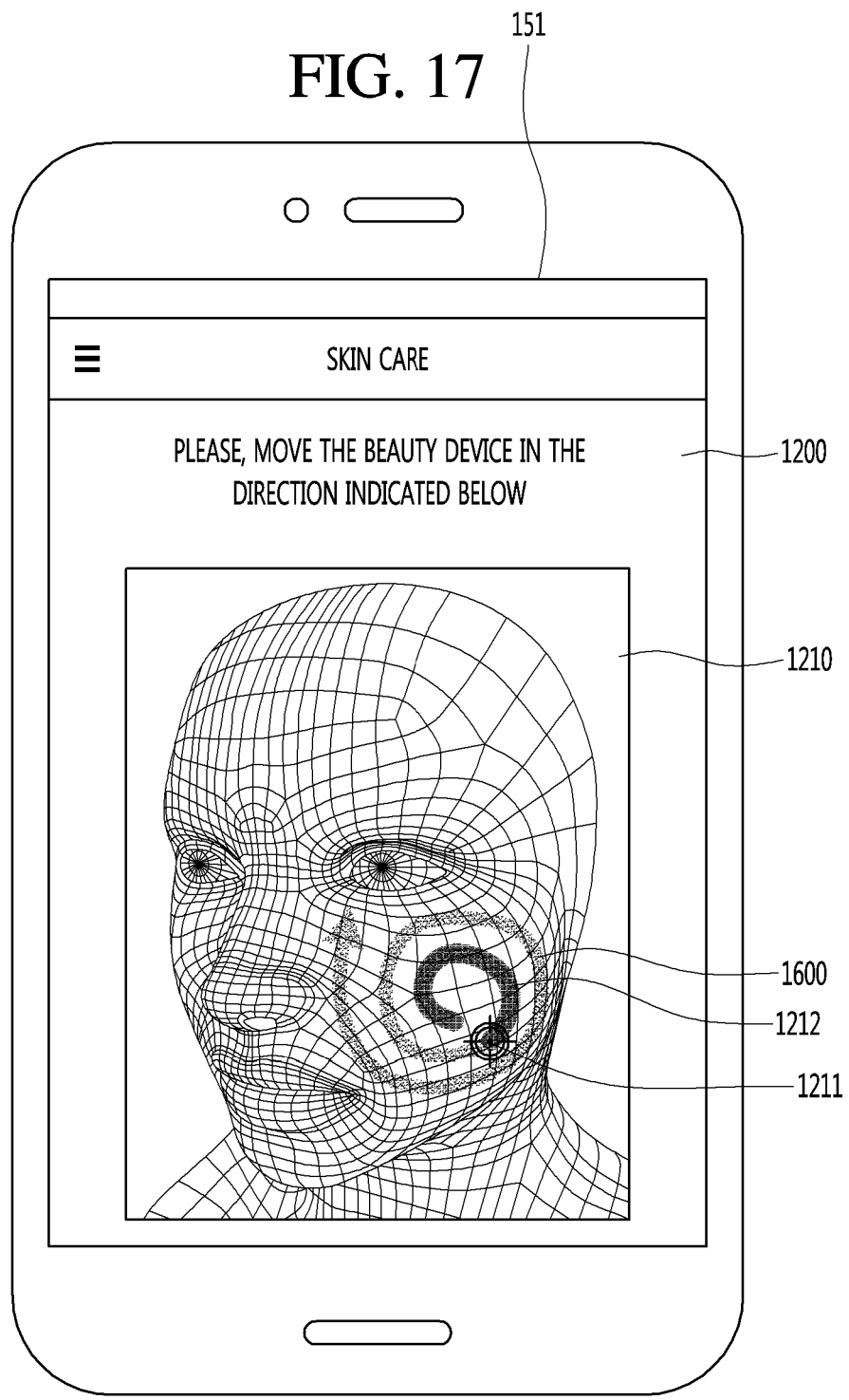

As illustrated in FIG. 17, the display unit 151 may display the care guide line 1600 and the care progress status mark 1212, which is moved along the care guide line 1600, in an overlapping manner. Since the user can confirm both the care guide line 1600 and the care progress status mark 1212 at the same time, the user can confirm in real time whether the beauty device 200 is exactly moved along the care guide line 1600.

Figure 18:
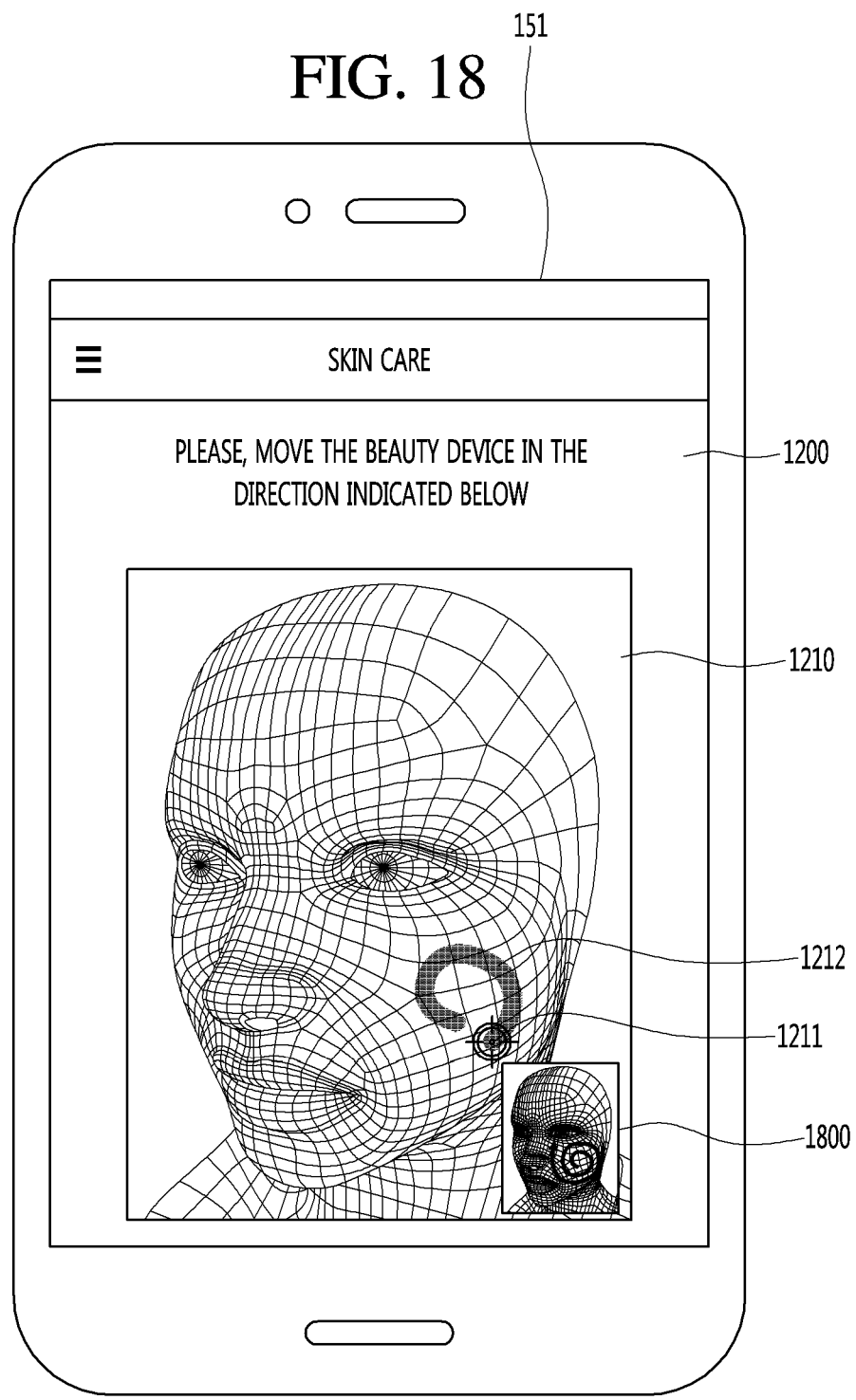

Alternatively, the display unit 151 may display the care guide line and the care progress status mark 1212 without overlapping each other. For example, as illustrated in FIG. 18, the display unit 151 may display a care guide line miniview 1800 in a portion of the care tracking screen 1200. Therefore, the user can distinctively confirm the care guide line and the care progress status mark without confusion.

In this manner, the user can confirm the part of the face, at which the beauty device 200 is located, on the display unit 151, in real time. Thus, the user can easily confirm which part of the face is being cared and which part of the face is required to be further cared.

Figure 19:
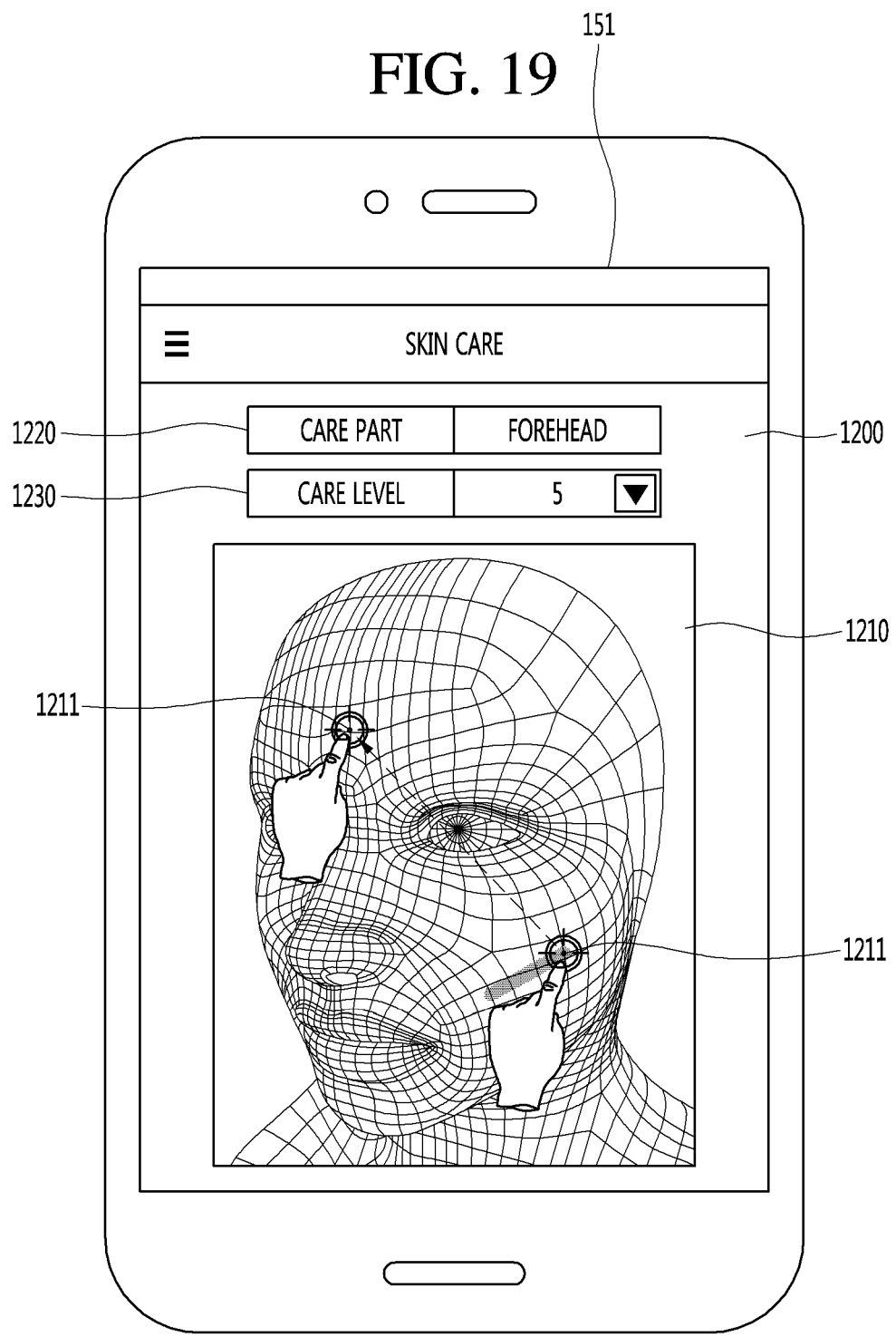

Also, in the case of displaying the care tracking screen 1200, the display unit 151 may display the care location mark 1211 at an incorrect position. For example, since there is an error in the curvature of each part of the face with respect to each person, the care location mark 1211 may be incorrectly displayed. In this case, the controller 180 may receive an instruction to change the care location mark 1211. For example, as illustrated in FIG. 19, the controller 180 may receive an instruction to select the care location mark 1211 and drag and drop the selected care location mark 1211 at a certain position. In this manner, the display unit 151 may display the care location mark 1211 moved to the certain position. When the position of the care location mark 1211 displayed on the display unit 151 is different from the position of the beauty device 200 touched on the user's face, the user can arbitrarily modify the care location mark 1211 by selecting the care location mark 1211 and dragging and dropping the selected care location mark 1211. When the care location mark 1211 is changed, the controller 180 may automatically change the care part 1220 and the care level 1230 so as to correspond to the changed position.

In accordance with another embodiment of the present disclosure, the care tracking screen 1200 may include the face photographed by the camera 121, not the face simulation 1210 as illustrated in FIGS. 12 to 19. In this case, the display unit 151 may further display the care progress status with a skin whitening effect on the face, not the care progress status mark 1212. Specifically, the display unit 151 may notify the user of the care progress status by more gaily displaying the part of the face being cared by the beauty device 200. In this manner, the user can be helped to feel the effect of the beauty device 200 more realistically.

Referring again to FIG. 11, the controller 180 may sense a state in which the movement of the beauty device 200 has been stopped for more than a certain time (S211).

The controller 180 may continuously sense the movement of the beauty device 200 based on the location information of the beauty device 200 that is received from the beauty device 200. Therefore, the controller 180 may sense the state in which the movement of the beauty device 200 is stopped. Alternatively, the controller 180 may recognize that the location information has not been received from the beauty device 200 for more than a certain time. In this manner, the controller 180 may sense the state in which the movement of the beauty device 200 has been stopped for more than a preset time.

When the controller 180 senses the state in which the movement of the beauty device 200 is stopped, the controller 180 may display a notification message related to a part on which the care operation is not completed (S213).

Next, the operation of displaying the notification message related to the part on which the care operation is not completed, in accordance with an embodiment of the present disclosure, will be described with reference to FIG. 20.

Figure 20:
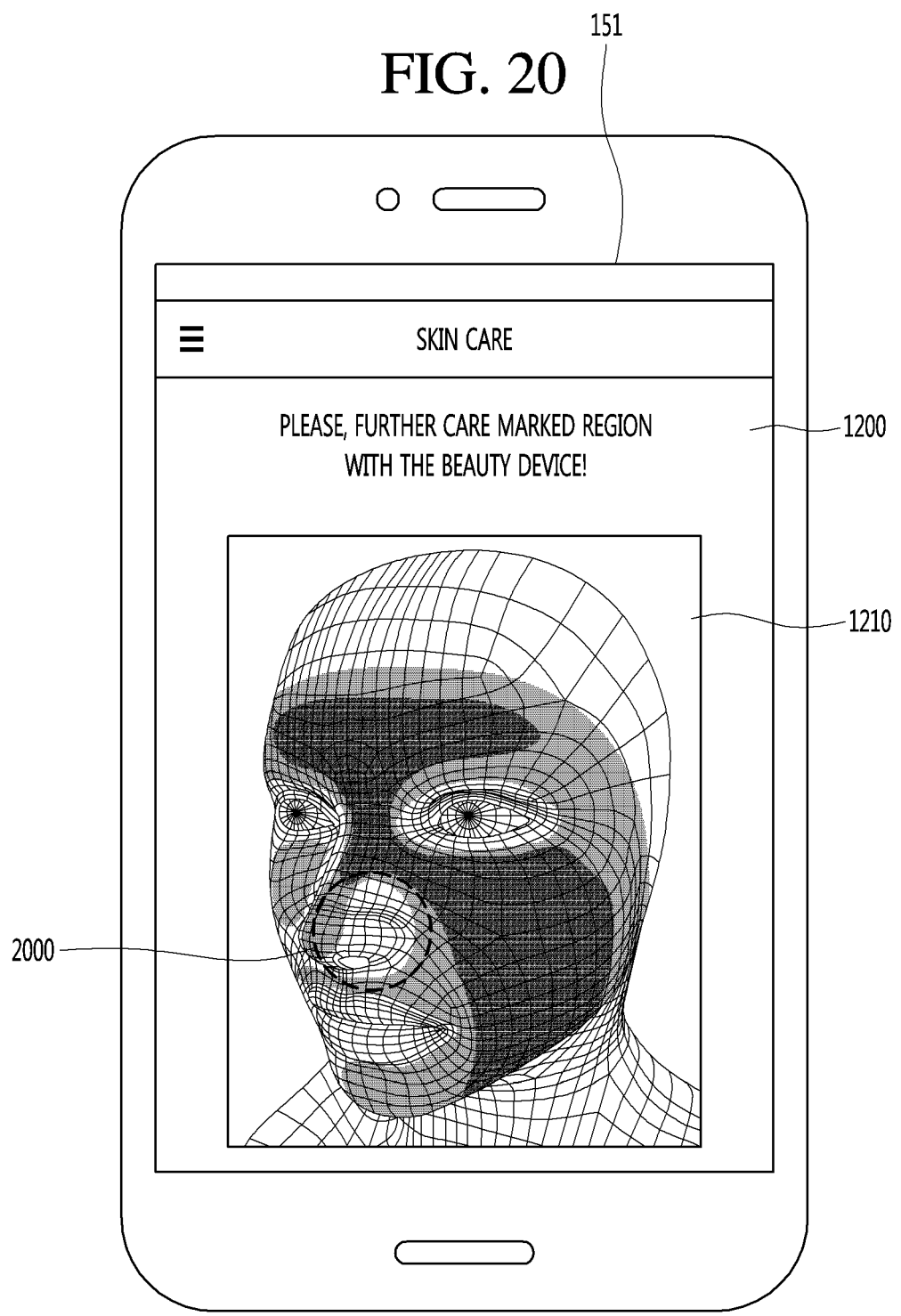
FIG. 20 is a diagram for describing an operation of displaying a notification message related to a part on which a care operation is not completed, in accordance with an embodiment of the present disclosure.

FIG. 20 is a diagram for describing the operation of displaying the notification message related to the part on which the care operation is not completed, in accordance with an embodiment of the present disclosure.

When the controller 180 senses the state in which the movement of the beauty device 200 is stopped, the controller 180 may control the display unit 151 to display the notification message on the care tracking screen 1200. When the controller 180 senses the state in which the movement of the beauty device 200 is stopped, the controller 180 acquires the part on which the care operation is not completed in the face simulation 1210. The display unit 151 may display a care non-completion part notification 2000 and a notification message related thereto, for example "Please, further care the displayed part with the beauty device!". The user can know see the care non-completion part notification 2000 displayed on the care tracking screen 1200 and know that the user has to further care the corresponding part before completing the care. Therefore, the user can be helped to care the entire face uniformly.

Referring again to FIG. 11, when the controller 180 does not sense the state in which the movement of the beauty device 200 has been stopped for more than the certain time, the controller 180 may determine whether an instruction to select the end of the care operation has been received (S215).

The controller 180 may continuously sense the movement of the beauty device 200. When the controller 180 senses the beauty device 200 as being continuously moving, the controller 180 may determine whether the instruction to select the end of the care operation has been received.

When the controller 180 determines that the instruction to select the end of the care operation has not been received, the controller 180 may proceed to operation S203 to receive the location information of the beauty device 200 from the beauty device 200.

Alternatively, the controller 180 may receive the instruction to select the end of the care operation. For example, when the controller 180 receives an instruction to select a power button (not illustrated) provided in the beauty device 200, the controller 180 may determine that the instruction to select the end of the care operation is received. Alternatively, when the controller 180 receives an instruction to select a care end icon (not illustrated) displayed on the display unit 151, the controller 180 may determine that the instruction to select the end of the care operation is received.

When the controller 180 determines that the instruction to select the end of the care operation is received, the controller 180 may control the display unit 151 to display a care completion screen (S217).

Next, a care completion screen in accordance with an embodiment of the present disclosure will be described with reference to FIGS. 21 and 22.

Figure 21:
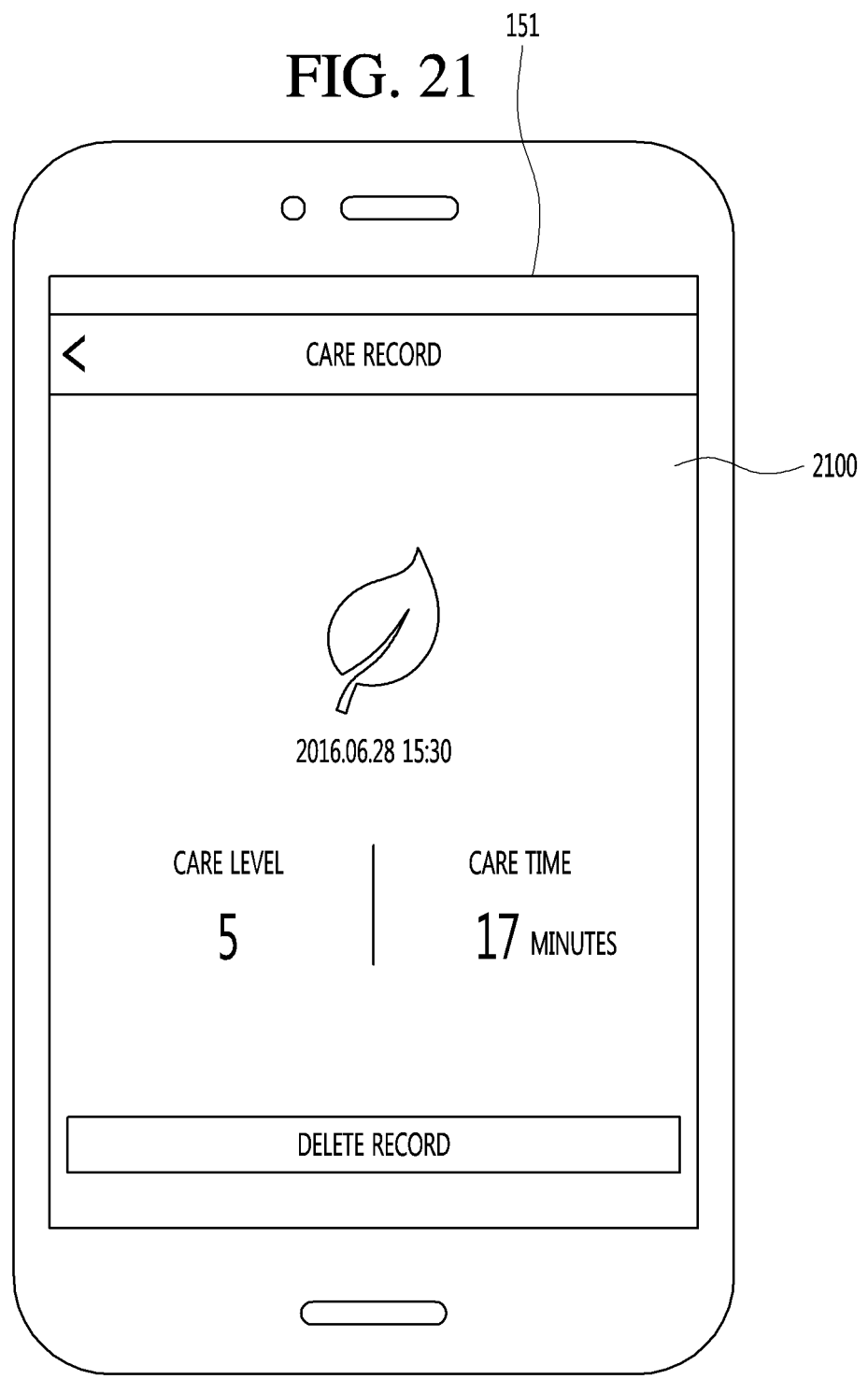
FIG. 21 is a diagram for describing a care completion screen in accordance with an embodiment of the present invention.

FIG. 21 is a diagram for describing a care completion screen in accordance with an embodiment of the present invention.

The display unit 151 may display the care completion screen 2100. The care completion screen 2100 may include at least one of a care date, a care level, a care time, and a record deletion icon. The care date may mean a date when the care operation was performed with the beauty device 200. The care level may mean an average care level of the care operation. Alternatively, the care level may mean a care level when the care operation was ended. The care time may mean a care operation execution time indicating how long the user performed the care operation. The record deletion icon may mean an icon for performing control so that the record of the corresponding care operation is not stored.

Figure 22:
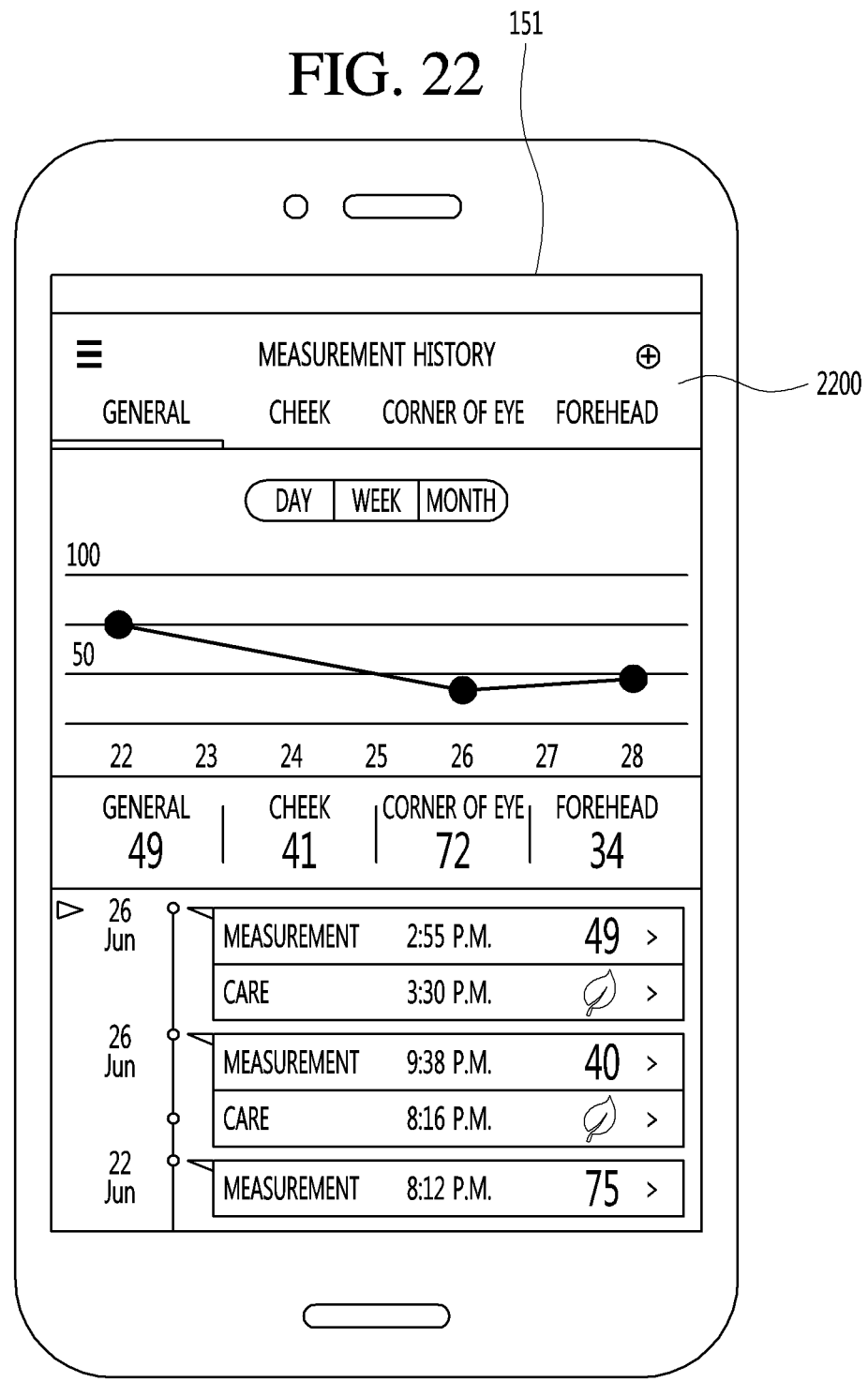
FIG. 22 is a diagram for describing a measurement history screen in accordance with an embodiment of the present invention.

FIG. 22 is a diagram for describing a measurement history screen in accordance with an embodiment of the present invention. When an instruction to select the measurement history icon 913 included in the skin measurement result screen 900 is received, the measurement history screen 2200 may be displayed on the display unit 151. Alternatively, when the care operation is ended, the measurement history screen 2200 may be displayed on the display unit 151. The measurement history screen 2200 may include a graph of a result measured for the last one week, scores, and an icon indicating whether the care by date was performed. While viewing the measurement history screen 2200, the user can know a change in the skin condition for the last one week and can confirm how much the user has recently been cared.

Next, a care level correction screen in accordance with an embodiment of the present disclosure will be described with reference to FIGS. 23 to 26.

Figure 23:
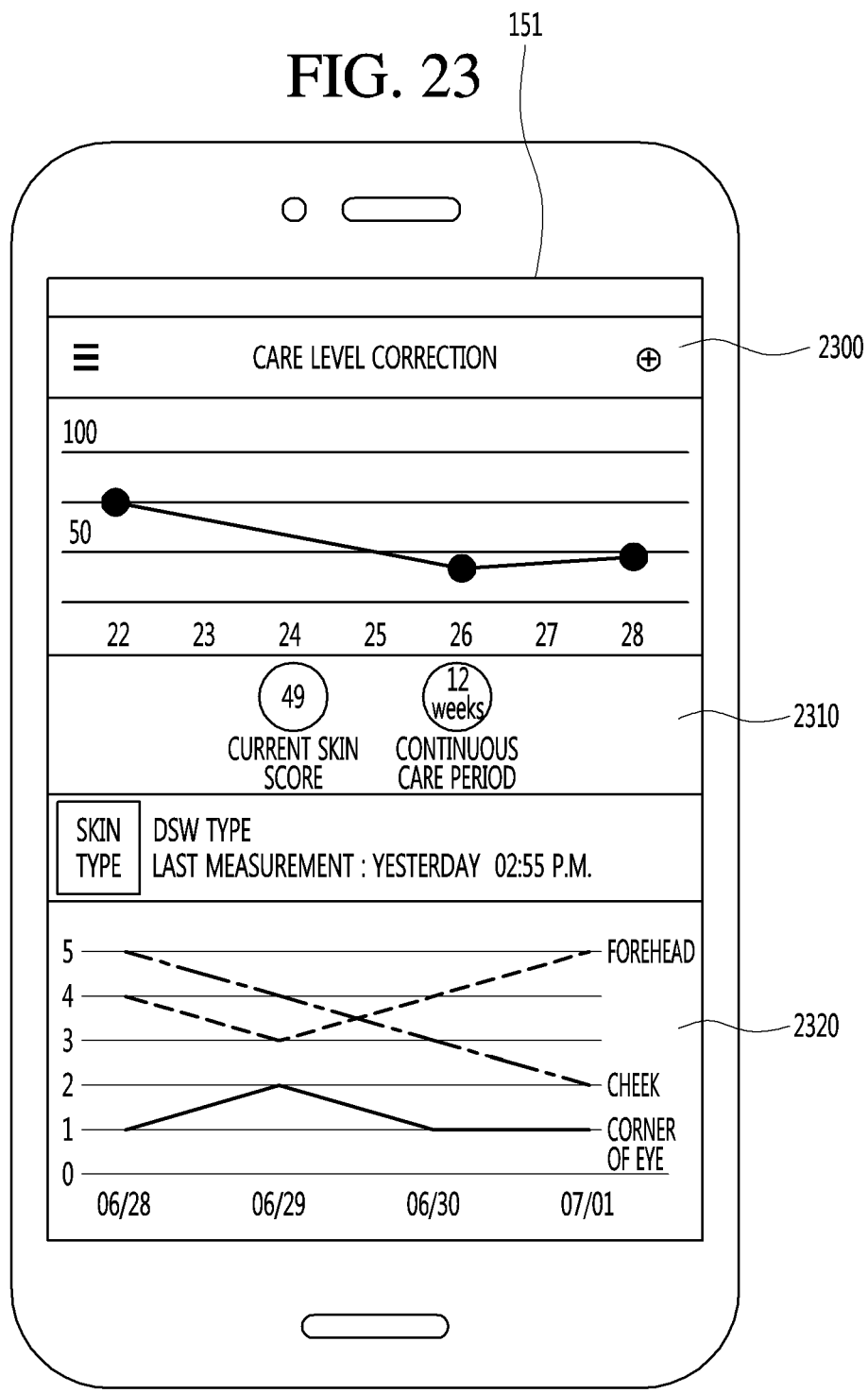
FIG. 23 is a diagram for describing a care level correction screen based on a measurement history in accordance with an embodiment of the present invention.

FIG. 23 is a diagram for describing a care level correction screen based on a measurement history in accordance with an embodiment of the present invention.

The display unit 151 may display the care level correction screen 2300 for correcting the care level based on the measurement history. The care level correction screen 2300 based on the measurement history may include a measurement history 2310 and a recommended care level 2320. The measurement history 2310 may include a skin condition measurement score for the last one week, a current skin condition measurement score, and a skin type. The recommended care level 2320 may include recommended care levels for each part of the face, which correspond to tomorrow, the day after tomorrow, and two days after tomorrow with respect to today's date, based on the measurement history 2310. In a case where the care operation is performed tomorrow, the day after tomorrow, and two days after tomorrow, the controller 180 may set the care operations to be performed according to the recommended care levels.

Figure 24:
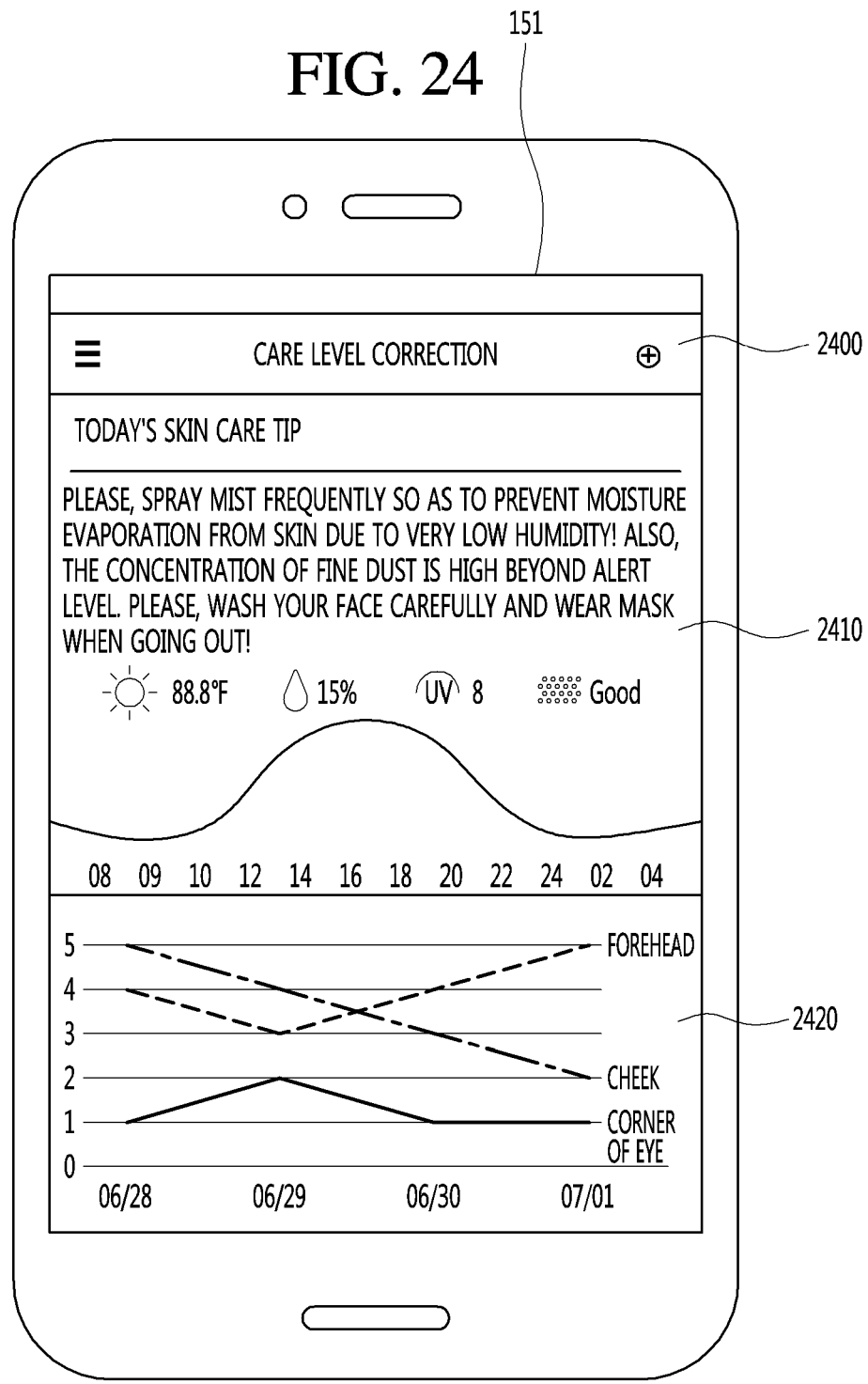
FIG. 24 is a diagram for describing a care level correction screen based on weather in accordance with an embodiment of the present invention.

FIG. 24 is a diagram for describing a care level correction screen based on weather in accordance with an embodiment of the present invention.

The display unit 151 may display the care level correction screen 2400 based on weather. The care level correction screen 2400 based on the weather may include weather information 2410 and a recommended care level 2420. The weather information 2410 may include weather information provided by a weather center. Alternatively, the weather information 2410 may include current weather information considering a skin care. Therefore, the weather information 2410 may include a temperature, a humidity, an ultraviolet (UV) index, and the like. The recommended care level 2420 is similar to that described above with reference to FIG. 23 and may include recommended care levels for each part of the face, which correspond to tomorrow, the day after tomorrow, and two days after tomorrow with respect to today's date, based on the weather information.

Figure 25:
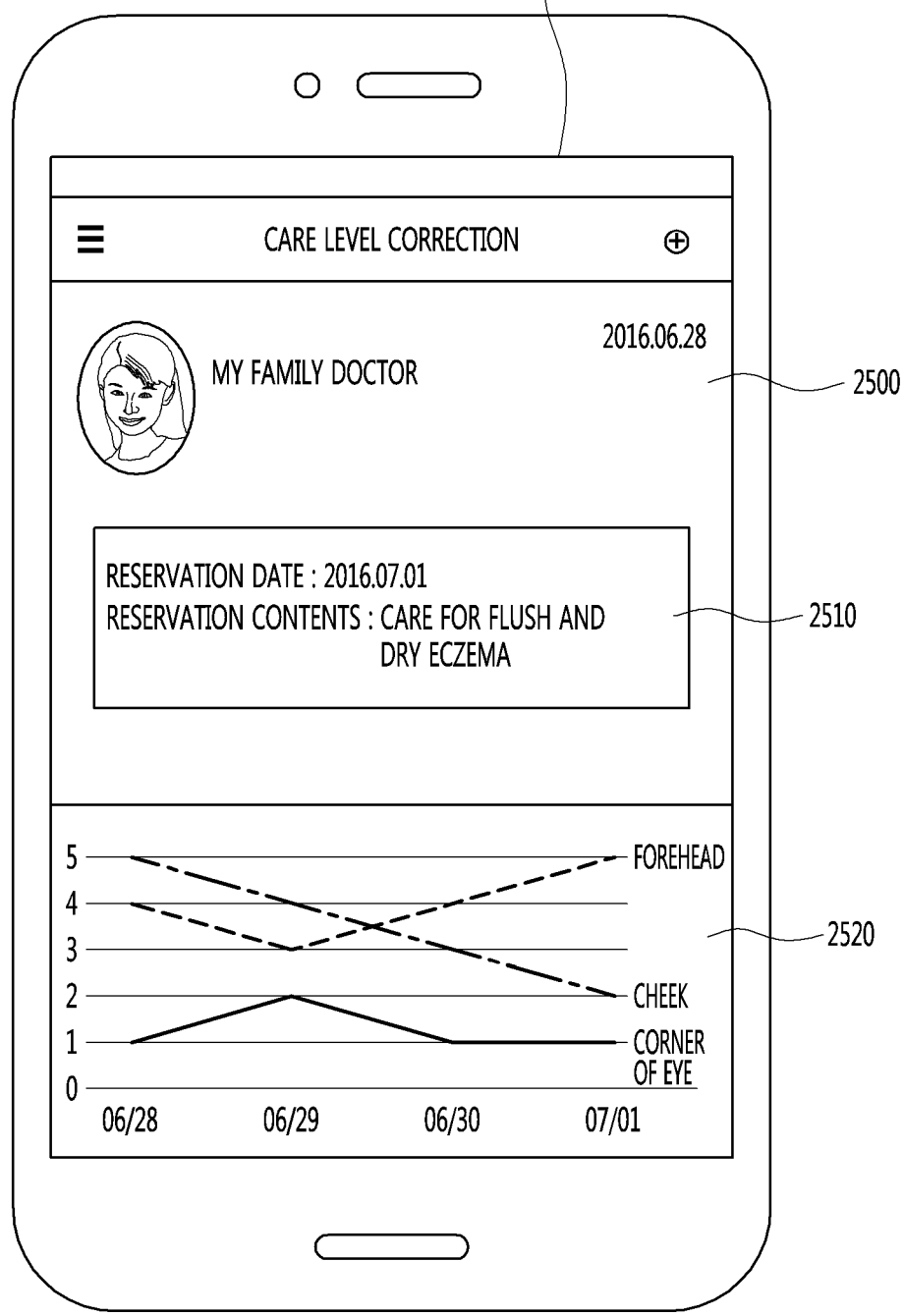
FIG. 25 is a diagram for describing a care level correction screen based on dermatological records in accordance with an embodiment of the present invention.

FIG. 25 is a diagram for describing a care level correction screen based on dermatological records in accordance with an embodiment of the present invention.

The display unit 151 may display the care level correction screen 2500 based on dermatological records. The care level correction screen 2500 based on the dermatological records may include a dermatological treatment table 2510 and a recommended care level 2520. The dermatological treatment table 2510 may include a user's past dermatological records and a user's treatment schedule records. The contents described in the dermatological treatment table 2510 may be contents written by a user input. The recommended care level 2520 is similar to that described above with reference to FIG. 23 and may include recommended care levels for each part of the face, which correspond to tomorrow, the day after tomorrow, and two days after tomorrow with respect to today's date, based on the user's past dermatological records and the user's treatment schedule records.

FIG. 26 is a diagram for describing a care level correction screen based on used cosmetics in accordance with an embodiment of the present invention.

The display unit 151 may display the care level correction screen 2600 based on the used cosmetics. The care level correction screen 2600 based on the used cosmetics may include a used cosmetics list 2610 and a recommended care level 2620. The used cosmetics list 2610 may be made by a reception of a user input. The controller 180 may set recommended care levels for each part of the face based on components of at least one cosmetics included in the used cosmetics list. The recommended care level 2620 is similar to that described above with reference to FIG. 23 and may include recommended care levels for each part of the face, which correspond to tomorrow, the day after tomorrow, and two days after tomorrow with respect to today's date, based on the cosmetics used by the user.

In accordance with at least one of the embodiments of the present disclosure, when the user measures the skin condition or performs the care operation through the beauty device, the user can freely use the beauty device without following the instruction displayed on the mobile terminal.

In accordance with at least one of the embodiments of the present disclosure, when the user performs the care operation through the beauty device, the user can confirm which part of the face is currently cared through the screen of the mobile terminal.

In accordance with at least one of the embodiments of the present disclosure, when the user performs the care operation through the beauty device, the user can be notified of the required degree of care for each part of the face and the progress status of the care operation.

In accordance with at least one of the embodiments of the present disclosure, the method of performing effective care through the beauty device can be provided to the user.

In accordance with at least one of the embodiments of the present disclosure, it is possible to provide the method of completely care the entire face by notifying the user of the insufficiently cared part of the face.

In accordance with at least one of the embodiments of the present disclosure, it is possible to provide the user customized care method considering care frequency, weather, dermatological treatment, used cosmetics, and the like.

The present invention mentioned in the foregoing description may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A mobile terminal comprising:
    a wireless communication unit;
    a memory in which a plurality of curvature ranges are stored, wherein each of the plurality of curvature ranges corresponds to a section of a face such that each curvature range corresponding to a specific section of the face is different from other curvature ranges corresponding to other sections of the face;
    a display; and
    a controller configured to:
        receive location information from an auxiliary device via the wireless communication unit, wherein the location information includes curvature information of a part of a face of a user that is in contact with the auxiliary device and movement information of the auxiliary device relative to the user's face, wherein the curvature information includes a rate of variation indicating a degree of curvature of a surface of the face;
        acquire a curvature range, which includes the rate of variation received from the auxiliary device, from the memory;
        determine a section of the user's face corresponding to the acquired curvature range;
        recognize the part of the user's face that is in contact with the auxiliary device based on the determined section; and
        cause the display to display a simulated face, a care location mark indicated at a first position of the simulated face that corresponds to the recognized part, wherein the care location mark indicates a current location of the auxiliary device on the face of the user.

2. The mobile terminal of claim 1, wherein the controller is further configured to cause the display to display a care progress status on the simulated face in an overlapping manner, the care progress status indicating an area of the face through which the auxiliary device passes.

3. The mobile terminal of claim 2, wherein opacity of the care progress status is displayed differently based on a number of times the auxiliary device passes over a certain area of the face.

4. The mobile terminal of claim 3, wherein the opacity of the care progress status gets darker as the number of times the auxiliary device passes over the certain area increases.

5. The mobile terminal of claim 2, wherein opacity of the care progress status is displayed differently to indicate how much care is required for the face.

6. The mobile terminal of claim 5, wherein the controller is further configured to cause the display to:
   display an area of the face requiring high-intensity care with light opacity; and
   display an area of the face requiring low-intensity care with dark opacity.

7. The mobile terminal of claim 2, wherein the controller is further configured to cause the display to display the care progress status distinguishably for different parts of the face when the part of the face, at which the auxiliary device is located, is changed.

8. The mobile terminal of claim 2, wherein the controller is further configured to cause the display to display a care guide line on the simulated face, the care guide line indicating a recommended care method for parts of the face.

9. The mobile terminal of claim 1, wherein the controller is further configured to:
   receive an input for selecting the care location mark, the input comprising dragging to and dropping the selected care location mark at a second position of the simulated face; and
   cause the display to display the care location mark at the second position in response to the received input.

10. The mobile terminal of claim 1, wherein the controller is further configured to cause the display to display a notification message indicating that care of the part of the face has not been completed when the auxiliary device has not been moved for more than a threshold period of time.

11. The mobile terminal of claim 1, wherein the auxiliary device comprises a wireless communication unit configured to transmit the location information to the mobile terminal.

12. The mobile terminal of claim 11, wherein the auxiliary device further comprises a measurement unit configured to measure a skin condition of the user.

13. The mobile terminal of claim 12, wherein the auxiliary device further comprises a sensor configured to generate the location information by contacting the face.

14. The mobile terminal of claim 1, wherein the controller is further configured to recognize a part of the face where a care operation by the auxiliary device has not been completed.

15. The mobile terminal of claim 14, wherein the controller is further configured to cause the display to display a message informing that further care operation needs to be performed by the auxiliary device at the part of the face where the care operation has not been completed.

16. The mobile terminal of claim 1, wherein the controller is further configured to cause the display to display a picture of the face received via a camera instead of the simulated face based on a setting such that the care location mark is indicated on the picture of the face.

17. The mobile terminal of claim 1, wherein the plurality of curvature ranges are pre-stored in the memory.

* * * * *